(12) United States Patent
Chambers

(10) Patent No.: US 8,101,378 B2
(45) Date of Patent: *Jan. 24, 2012

(54) DUAL EXPRESSION VECTOR SYSTEM AND SCREENING METHODS

(75) Inventor: Stephen P. Chambers, Belmont, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 192 days.

This patent is subject to a terminal disclaimer.

(21) Appl. No.: 12/355,880

(22) Filed: Jan. 19, 2009

(65) Prior Publication Data

US 2010/0248304 A1 Sep. 30, 2010

Related U.S. Application Data

(63) Continuation of application No. 11/033,774, filed on Jan. 12, 2005, now Pat. No. 7,498,166.

(60) Provisional application No. 60/535,851, filed on Jan. 12, 2004.

(51) Int. Cl.
*C12P 21/02* (2006.01)
(52) U.S. Cl. .............. 435/69.1; 435/320.1; 435/252.33; 435/348
(58) Field of Classification Search ................ None
See application file for complete search history.

(56) References Cited

U.S. PATENT DOCUMENTS

| 5,939,285 | A | 8/1999 | Devauchelle et al. |
| 6,589,783 | B2 | 7/2003 | Novy et al. |
| 7,498,166 | B2 * | 3/2009 | Chambers ................ 435/320.1 |
| 2002/0160507 | A1 | 10/2002 | Novy et al. |

OTHER PUBLICATIONS

International Search Report received in corresponding PCT Application No. PCT/US2005/000922, (2006).
Lee et al., "Identification of a very early promoter of insect Hz-1 virus using a novel dual-expression shuttle vector", Nucleic Acids Research 23(22):4683-4689, (1995).

* cited by examiner

*Primary Examiner* — Jim Ketter
(74) *Attorney, Agent, or Firm* — Michele A. Kercher; Kumar Govindaswamy; Vertex Pharmaceuticals Incorporated

(57) ABSTRACT

The present invention features vectors that contain a promoter effective for expression in bacterial cells and a promoter effective for expression in insect cells. The dual promoter system allows use of the same vector in both host cell systems so that construction of only a single vector is needed to express a polynucleotide inserted at a downstream cloning site. In preferred embodiments the vector is used to derive a recombinant baculovirus that is used to infect host cells. In particular vectors the promoters are a baculovirus polh promoter and a T7lac promoter. In particular vectors the promoter effective for expression in bacteria is positioned between the promoter effective for expression in insect cells and a cloning site. The invention also features various high throughput screening methods.

9 Claims, 13 Drawing Sheets

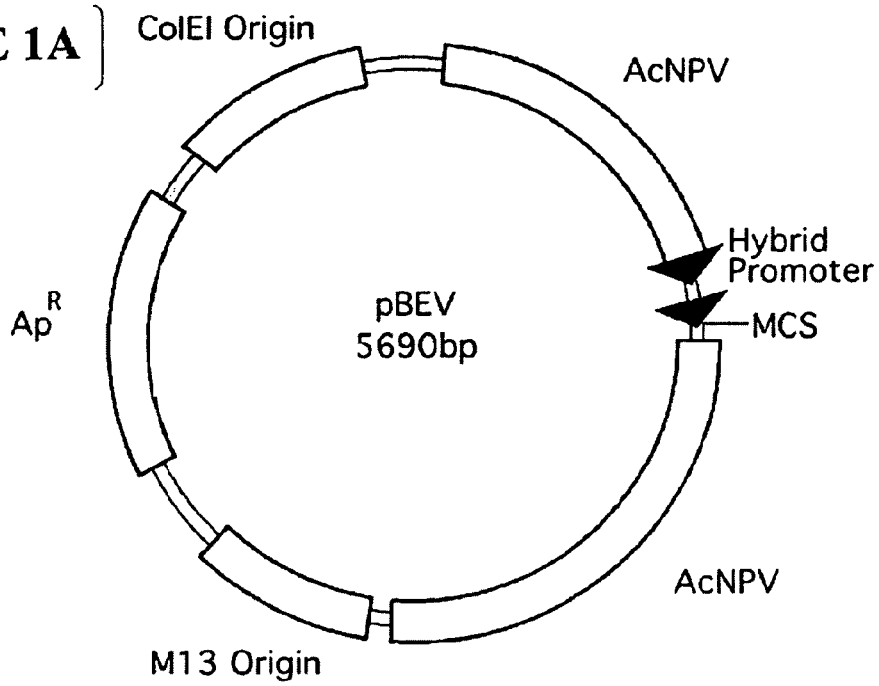

FIGURE 1A

```
                           polh promoter
AAATGTCTATCAATATATAGTTGCTGATATCATGGAGTAATTAAAATGATAACCATCT
         *polh mRNA  5' end
CGCAAATAAATAAGTATTTTACGTTTTCGTAACAGTTTTGTAATAAAAAAACTATAAA
T7 promoter            lac operator
TAATACGACTCACTATAGGGGAATTGTGAGCGGATAACAATTCCCCTCTAGAAATAAT
                       +87                  His-Tag
TTTGTTTAACTTTAAGAAGGAGATATACCATGGGCAGCAGCCATCATCATCATCATCAC
                                MetGlySerSerHisHisHisHisHisHis
         thrombin        NdeI   XhoI BamHI
AGCAGCGGCCTGGTGCCGCGCGGCAGCCATATGCTCGAGGATCCCTGCAGGCCTCGAGT
SerSerGlyLeuValProArgGlySerHisMet

TCGAATCTAGAAGATCTGGTACC
```

```
BASE COUNT     1494 a    1241 c    1313 g    1642 t
ORIGIN
    1 AACGGCTCCG CCCACTATTA ATGAAATTAA AAATTCCAAT TTTAAAAAAC GCAGCAAGAG
   61 AAACATTTGT ATGAAAGAAT GCGTAGAAGG AAAGAAAAAT GTCGTCGACA TGCTGAACAA
  121 CAAGATTAAT ATGCCTCCGT GTATAAAAAA AATATTGAAC GATTTGAAAG AAAACAATGT
  181 ACCGCGCGGC GGTATGTACA GGAAGAGGTT TATACTAAAC TGTTACATTG CAAACGTGGT
  241 TTCGTGTGCC AAGTGTGAAA ACCGATGTTT AATCAAGGCT CTGACGCATT TCTACAACCA
  301 CGACTCCAAG TGTGTGGGTG AAGTCATGCA TCTTTTAATC AAATCCCAAG ATGTGTATAA
  361 ACCACCAAAC TGCCAAAAAA TGAAAACTGT CGACAAGCTC TGTCCGTTTG CTGGCAACTG
  421 CAAGGGTCTC AATCCTATTT GTAATTATTG AATAATAAAA CAATTATAAA TGCTAAATTT
  481 GTTTTTTATT AACGATACAA ACCAAACGCA TATTTAAAAT TTGTAGTATT ATCTATAATT
  541 GAAAACGCGT AGTTATAATC GCTGAGGTAA CATTTTCAAA CATTTTCAAA TGATTCACAG
  601 TTAATTGCG ACAATATAAT TTTATTTCA CATAAACTAG ACGCCTTGTC GTCTTCTTCT
  661 TCGTATTCCT TCTCTTTTTC ATTTTCTCC TCATAAAAAT TAACATAGTT ATTATCGTAT
  721 CCATATATGT ATCTATCGTA TAGAGTAAAT TTTTGTTGT CATAAAATAA TATGTCTTTT
  781 TTAATGGGGT GTATAGTACC GCTGCGCATA GTTTTTCTGT AATTACAAC AGTGCTATTT
  841 TCTGGTAGTT CTTCGGAGTG TGTTGCTTTA ATTATTAAAT TTATATAAAT AATGAATTTG
  901 GGATCGTCGG TTTTGTACAA TATGTTGCCG GCATAGTACG CAGCTTCTTC TAGTTCAATT
  961 ACACCATTT TTAGCAGCAC CGGATTAACA TAACTTTCCA AAATGTTGTA CGAACCGTTA
 1021 AACAAAAACA GTTCACCTCC CTTTTCTATA CTATTGTCTG CGAGCAGTTG TTTGTTGTTA
 1081 AAAATAACAG CCATTGTAAT GAGACGCACA AACTAATATC ACAAACTGGA AATGTCTATC
 1141 AATATATAGT TGCTGATATC ATGGAGATAA TTAAAATGAT AACCATCTCG CAAATAAATA
 1201 AGTATTTTAC TGTTTTCGTA ACAGTTTGT AATAAAAAAA CCTATAAATA ATACGACTCA
 1261 CTATAGGGGA ATTGTGAGCG GATAACAATT CCCCTCTAGA AATAATTTTG TTTAACTTTA
 1321 AGAAGGAGAT ATACCATGGG CAGCAGCCAT CATCATCATC ATCACAGCAG CGGCCTGGTG
 1381 CCGCGCGGCA GCCATATGCT CGAGGATCCC TGCAGGCCTC GAGTTCGAAT CTAGAAGATC
 1441 TGGTACCGAG CTCGAATTCC CGGGCGGCCG CTTAATTAAT TGATCCGGGT TATTAGTACA
 1501 TTTATTAAGC GCTAGATTCT GTGCGTTGTT GATTACAGA CAATTGTTGT ACGTATTTTA
 1561 ATAATTCATT AAATTTATAA TCTTTAGGGT GGTATGTTAG AGCGAAAATC AAATGATTTT
```

Figure 1C-2

```
1621 CAGCGTCTTT ATATCTGAAT TTAAATATTA AATCCTCAAT AGATTTGTAA AATAGGTTTC
1681 GATTAGTTTC AAACAAGGGT TGTTTTTCCG AACCGATGGC TGGACTATCT AATGGATTTT
1741 CGCTCAACGC CACAAAACTT GCCAAATCTT GTAGCAGCAA TCTAGCTTTG TCGATATTCG
1801 TTTGTGTTTT GTTTTGTAAT AAAGGTTCGA CGTCGTTCAA AATATTATGC GCTTTTGTAT
1861 TTCTTTCATC ACTGTCGTTA GTGTACAATT GACTCGACGT AAACACGTTA AATAAAGCTT
1921 GGACATATTT AACATCGGGC GTGTTAGCTT TATTAGGCCG ATTATCGTCG TCGTCCCAAC
1981 CCTCGTCGTT AGAAGTTGCT TCCGAAGACG ATTTTGCCAT AGCCACACGA CGCCTATTAA
2041 TGTGTCGGC TAACACGTCC GCGATCAAAT TTGTAGTTGA GCTTTTTGA ATTATTCTG
2101 ATTGCGGGCG TTTTTGGGCG GGTTTCAATC TAACTGTGCC CGATTTTAAT TCAGACAACA
2161 CGTTAGAAAG CGATGGTGCA GGCGGTGGTA ACATTTCAGA CGGCAAATCT ACTAATGGCG
2221 GCGGTGGTGG AGCTGATGAT AAATCTACCA TCGGTGGAGG CGCAGGCGGG GCTGGCGGCG
2281 GAGGCGGAGG CGGAGGTGGT GGCGGTGATG CAGACGGCGG TTTAGGCTCA AATGTCTCTT
2341 TAGGCAACAC AGTCGGCACC TCAACTATTG TACTGTTTC GGGCGCCGTT TTTGGTTTGA
2401 CCGGTCTGAG ACGAGTGCGA TTTTTTTCGT TTCTAATAGC TTCCAACAAT TGTTGTCTGT
2461 CGTCTAAAGG TGCAGCGGGT TGAGGTTCCG TGGGCATTGG TGGAGCGGGC GGCAATTCAG
2521 ACATCGATGG TGGTGGTGGT GGTGGAGGCG CTGGAATGTT AGGCACGGGA GAAGGTGGTG
2581 GCGGCGGTGC CGCCGGTATA ATTTGTTCTG GTTTAGTTTG TTCGCGCACG ATTGTGGGCA
2641 CCGGCGCAGG CGCGCCTGGC TGCACAACGG AAGGTCGTCT GCTTCGAGGC AGCGCTTGGG
2701 GTGGTGGCAA TTCAATATTA TAATTGGAAT ACAAATCGTA AAAATCTGCT ATAAGCATTG
2761 TAATTTCGCT ATCGTTTACC GTGCCGATAT TTAACAACCG CTCAATGTAA GCAATTGTAT
2821 TGTAAAGAGA TTGTCTCAAG CTCGGATCGA TCCCGCACGC CGATAACAAG CCTTTTCATT
2881 TTTACTACAG CATTGTAGTG GCGAGACACT TCGCTGTCGT CGCCTGATGC GGTATTTCT
2941 CCTTACGCAT CTGTGCGGTA TTTCACACCG CATACGTCAA AGCAACCATA GTACGCGCCC
3001 TGTAGCGGCG CATTAAGCGC GGCGGGTGTG GTGGTTACGC GCAGCGTGAC CGCTACACTT
3061 GCCAGCCCGC TAGCGCCCGC TCCTTTCGCT TTCTTCCCTT CCTTTCTCGC CACGTTCGCC
3121 GGCTTTCCCC GTCAAGCTCT AAATCGGGGG CTCCCTTTAG GGTTCCGATT TAGTGCTTTA
3181 CGGCACCTCG ACCCCAAAAA ACTTGATTTG GGTGATGGTT CACGTAGTGG GCCATCGCCC
3241 TGATAGACGG TTTTTCGCCC TTTGACGTTG GAGTCCACGT TCTTTAATAG TGGACTCTTG
3301 TTCCAAACTG GAACAACACT CAACCCTATC TCGGGCTATT CTTTGATTT ATAAGGATT
3361 TTGCCGATTT CGGCCTATTG GTTAAAAAAT GAGCTGATTT AACAAAAATT TAACGCGAAT
3421 TTTAACAAAA TATTAACGTT TACAATTTTA TGGTGCACTC TCAGTACAAT CTGCTCTGAT
```

Figure 1C-3

```
3481 GCCGCATAGT TAAGCCAGCC CCGACACCCG CCAACACCCG CTGACGCGCC CTGACGGGCT
3541 TGTCTGCTCC CGGCATCCGC TTACAGACAA GCTGTGACCG TCTCCGGGAG CTGCATGTGT
3601 CAGAGGTTTT CACCGTCATC ACCGAAACGC GCGAGACGAA AGGGCCTCGT GATACGCCTA
3661 TTTTTATAGG TTAATGTCAT GATAATAATG GTTTCTTAGA CGTCAGGTGG CACTTTTCGG
3721 GGAAATGTGC GCGGAACCCC TATTTGTTTA TTTTTCTAAA TACATTCAAA TATGTATCCG
3781 CTCATGAGAC AATAACCCTG ATAAATGCTT CAATAATATT GAAAAAGGAA GAGTATGAGT
3841 ATTCAACATT TCCGTGTCGC CCTTATTCCC TTTTTTGCGG CATTTTGCCT TCCTGTTTTT
3901 GCTCACCCAG AAACGCTGGT GAAAGTAAAA GATGCTGAAG ATCAGTTGGG TGCACGAGTG
3961 GGTTACATCG AACTGGATCT CAACAGCGGT AAGATCCTTG AGAGTTTTCG CCCCGAAGAA
4021 CGTTTTCCAA TGATGAGCAC TTTTAAAGTT CTGCTATGTG GCGCGGTATT ATCCGTATT
4081 GACGCCGGGC AAGAGCAACT CGGTCGCCGC ATACACTATT CTCAGAATGA CTTGGTTGAG
4141 TACTCACCAG TCACAGAAAA GCATCTTACG GATGGCATGA CAGTAAGAGA ATTATGCAGT
4201 GCTGCCATAA CCATGAGTGA TAACACTGCG GCCAACTTAC TTCTGACAAC GATCGGAGGA
4261 CCGAAGGAGC TAACCGCTTT TTTGCACAAC ATGGGGGATC ATGTAACTCG CCTTGATCGT
4321 TGGGAACCGG AGCTGAATGA AGCCATACCA AACGACGAGC GTGACACCAC GATGCCTGTA
4381 GCAATGGCAA CAACGTTGCG CAAACTATTA ACTGGCGAAC TACTTACTCT AGCTTCCCGG
4441 CAACAATTAA TAGACTGGAT GGAGGCGGAT AAAGTTGCAG GACCACTTCT GCGCTCGGCC
4501 CTTCCGGCTG GCTGGTTTAT TGCTGATAAA TCTGGAGCCG GTGAGCGTGG GTCTCGCGGT
4561 ATCATTGCAG CACTGGGGCC AGATGGTAAG CCCTCCCGTA TCGTAGTTAT CTACACGACG
4621 GGGAGTCAGG CAACTATGGA TGAACGAAAT AGACAGATCG CTGAGATAGG TGCCTCACTG
4681 ATTAAGCATT GGTAACTGTC AGACCAAGTT TACTCATATA TACTTTAGAT TGATTTAAAA
4741 CTTCATTTTT AATTTAAAAG GATCTAGGTG AAGATCCTTT TTGATAATCT CATGACCAAA
4801 ATCCCTTAAC GTGAGTTTTC GTTCCACTGA GCGTCAGACC CCGTAGAAAA GATCAAAGGA
4861 TCTTCTTGAG ATCCTTTTTT TCTGCGCGTA ATCTGCTGCT TGCAAACAAA AAAACCACCG
4921 CTACCAGCGG TGGTTTGTTT GCCGGATCAA GAGCTACCAA CTCTTTTTCC GAAGGTAACT
4981 GGCTTCAGCA GAGCGCAGAT ACCAAATACT GTCCTTCTAG TGTAGCCGTA GTTAGGCCAC
5041 CACTTCAAGA ACTCTGTAGC ACCGCCTACA TACCTCGCTC TGCTAATCCT GTTACCAGTG
5101 GCTGCTGCCA GTGGCGATAA GTCGTGTCTT ACCGGGTTGG ACTCAAGACG ATAGTTACCG
5161 GATAAGGCGC AGCGGTCGGG CTGAACGGGG GGTTCGTGCA CACAGCCCAG CTTGGAGCGA
5221 ACGACCTACA CCGAACTGAG ATACCTACAG CGTGAGCTAT GAGAAAGCGC CACGCTTCCC
5281 GAAGGGAGAA AGGCGGACAG GTATCCGGTA AGCGGCAGGG TCGAACAGG AGAGCGCACG
```

Figure 1C-4

```
5341 AGGGAGCTTC CAGGGGGAAA CGCCTGGTAT CTTTATAGTC CTGTCGGGTT TCGCCACCTC
5401 TGACTTGAGC GTCGATTTTT GTGATGCTCG TCAGGGGGGC GGAGCCTATG GAAAAACGCC
5461 AGCAACGCGG CCTTTTTACG GTTCCTGGCC TTTTGCTGGC CTTTTGCTCT CATGTTCTTT
5521 CCTGCGTTAT CCCCTGATTC TGTGGATAAAC CGTATTACCG CCTTTGAGTG AGCTGATACC
5581 GCTCGCCGCA GCCGAACGAC CGAGCGCAGC GAGTCAGTGA GCGAGGAAGC GGAAGAGCGC
5641 CCAATACGCA AACCGCCTCT CCCCGCGCGT TGGCCGATTC ATTAATGCAG
```

(SEQ ID NO: 2)

Figure 1D

ATCATGGAGTAATTAAAATGATAACCATCTCGCAAATAAATAAGTATTTTACGTTTTCGTAACA
GTTTTGTAATAAAAAAACTATAAATAATACGACTCACTATAGGGGAATTGTGAGCGGATAACAA
TTCCCCTCTAGAAATAATTTTGTTTAACTTTAAGAAGGAGATATACC (SEQ ID NO: 3)

Figure 1E

ATCATGGAGTAATTAAAATGATAACCATCTCGCAAATAAATAAGTATTTTACGTTTTCGTAACA
GTTTTGTAATAAAAAAACTATAAAT (SEQ ID NO: 4)

Figure 3A (top) and Figure 3B (bottom)
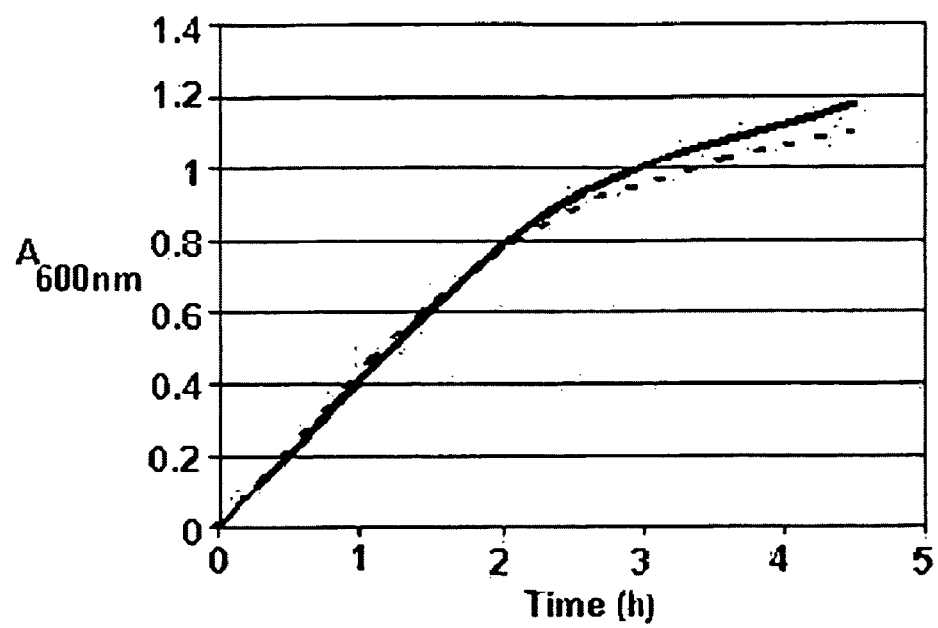
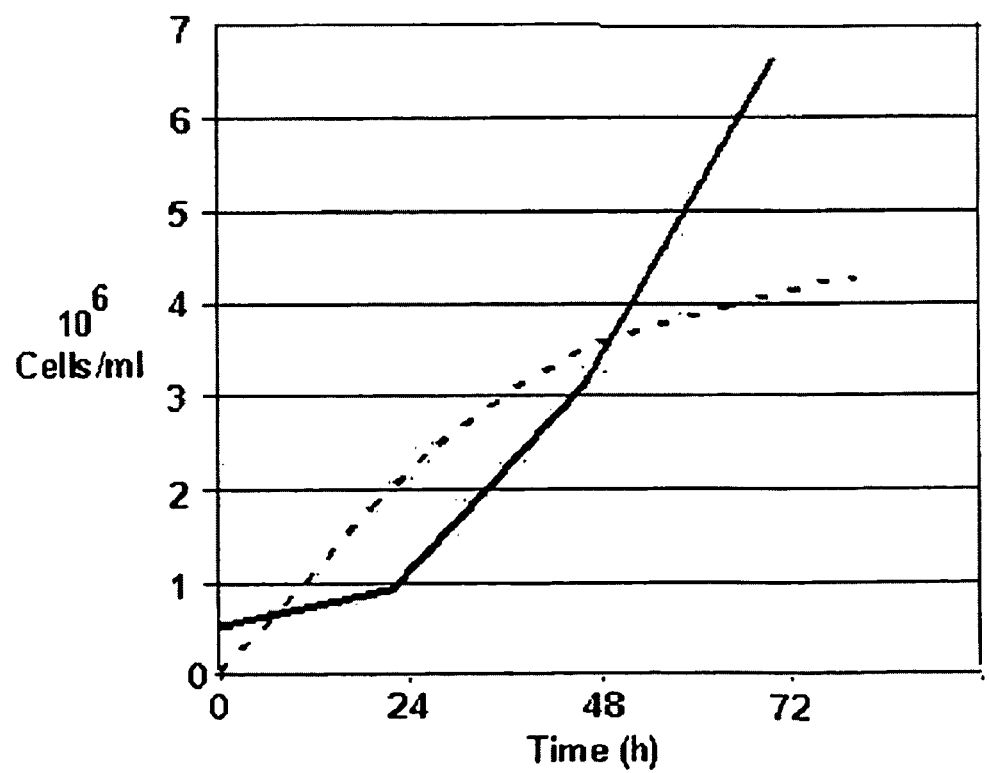

HT-Cloning & Expression Process

DUAL EXPRESSION VECTOR SYSTEM AND SCREENING METHODS

CROSS-REFERENCE TO RELATED APPLICATIONS

The present application is a continuation of U.S. patent application Ser. No. 11/033,774, filed Jan. 12, 2005 and entitled "DUAL EXPRESSION VECTOR SYSTEM AND SCREENING METHODS," which claims the benefit under 35 U.S.C. §119 of U.S. Provisional Application No. 60/535,851, filed Jan. 12, 2004 and entitled "DUAL EXPRESSION VECTOR SYSTEM AND SCREENING METHODS," the entire contents of each of the above applications are being incorporated herein by reference.

BACKGROUND OF THE INVENTION

Proteins produced in various host cells are used in a wide variety of applications. For example, such proteins are employed for experimental purposes such as determination of crystal structure and as antigens for raising antibodies. They are also used for an increasing number of therapeutic purposes. In general, the technology for producing proteins in host cells relies on polynucleotides referred to as expression vectors. These vectors are typically circular pieces of DNA known as plasmids, which may include various genetic elements to facilitate the expression of a protein coding sequence. Such elements typically include a promoter and may also include elements such as downstream transcription termination signals, polyadenylation signals, etc. In order to express a protein of interest, a polynucleotide that includes the coding sequence for the protein is inserted into the expression vector, e.g., at a specific location. The resulting vector is then introduced into host cells, which then express the protein of interest.

A wide variety of different host cells, ranging from prokaryotic cells such as *Escherichia coli* to eukaryotic cells, such as fungal (e.g., yeast), insect, mammalian, and plant cells are used for the production of proteins. The choice of host cell can be extremely important. For example, different host cells may synthesize the protein either more or less efficiently, which affects the final yield of product. In addition, certain proteins are soluble in certain host cells but insoluble in others. Proteins produced in eukaryotic cells are subject to a variety of post-translational modifications that do not occur in prokaryotic cells and may be needed for functional activity.

In general, different types of host cell frequently require different promoters. For example, many promoters that are utilized by prokaryotic host cells are inactive in eukaryotic hosts. Thus expression vectors are typically designed for use in a single host or class of hosts and contain appropriate genetic elements such as promoters for expression in that host or class of hosts. In order to express a protein of interest in multiple cell types, it is therefore typically necessary to construct multiple different expression vectors, each containing a sequence encoding the gene of interest and a promoter appropriate for expression in a different host cell. This can be inconvenient and time-consuming, particularly when there is a need to rapidly test multiple proteins in order to identify an appropriate host cell. Accordingly, there is a need in the art for a promoter that would function in multiple cell types and a need for an expression vector system that would allow expression of a protein of interest in multiple cell types. In addition, there is a need in the art for high throughput screening systems for proteins using multiple host cell types.

SUMMARY OF THE INVENTION

The present invention addresses the foregoing needs, among others. The invention provides a variety of expression vectors for expressing a polynucleotide, which may encode a protein of interest, in bacterial and insect host cells. In certain embodiments the inventive vectors feature a compact dual promoter region. The invention also provides screening methods, particularly high throughput screening methods, that may be used to select an appropriate host cell and/or culture condition.

In a first aspect, the invention provides a vector for expressing a protein in bacterial and insect host cells, the vector comprising: (i) first and second promoters, wherein the first promoter is effective to express a downstream protein coding sequence in insect host cells and the second promoter is effective to express the same downstream protein coding sequence in bacterial host cells; and (ii) a cloning site downstream of the promoters such that a protein coding sequence inserted into the site is transcribed in insect host cells and in bacterial host cells, wherein the second promoter is located between the first promoter and the cloning site.

The invention also provides a vector for expressing a protein in bacterial and insect host cells, the vector comprising: (i) first and second promoters, wherein the first promoter is a baculovirus polh promoter effective to express a downstream protein coding sequence in insect host cells expressing baculovirus proteins and the second promoter is effective to express the same downstream protein coding sequence in bacterial host cells; and (ii) a cloning site downstream of the promoters such that a protein coding sequence inserted into the site is transcribed in insect host cells expressing baculovirus proteins and in bacterial host cells, wherein the portion of the vector between the polh promoter and the cloning site comprises at least a portion of the polh mRNA 5' untranslated region, and wherein the portion of the polh mRNA 5' untranslated region is not immediately followed by a portion encoding a 5' portion of the Polh protein.

The invention also features a vector for expressing a protein in bacterial and insect host cells, the vector comprising: (i) first and second promoters, wherein the first promoter is effective to express a downstream protein coding sequence in insect host cells and the second promoter is effective to express the same downstream protein coding sequence in bacterial host cells; and (ii) a cloning site downstream of the promoters such that a protein coding sequence inserted into the site is transcribed in insect host cells and in bacterial host cells, wherein the promoters function with approximately equal efficacy in host cells cultured in volumes smaller than 5 ml and in volumes larger than 5 ml.

In another aspect, the invention provides a method of producing a protein of interest comprising steps of: (i) inserting a polynucleotide encoding a protein of interest into a cloning site of any of the inventive vectors; (ii) introducing the resulting vector, or a recombinant baculovirus derived from the vector into a host cell; (iii) culturing the host cell under conditions in which the protein is expressed; and (iv) harvesting the protein.

The invention also includes a method of identifying an appropriate host cell or production condition for producing a protein of interest comprising steps of: (i) inserting a polynucleotide encoding a protein of interest into a cloning site of an expression vector that comprises promoters effective for expression of the protein in both insect host cells and bacterial host cells; (ii) introducing the resulting vector into bacterial host cells; (iii) introducing a recombinant baculovirus derived from the resulting vector into insect host cells; (iv) culturing the bacterial and insect host cells; (v) purifying the protein from both bacterial and insect host cells; (vi) comparing the expression level and/or solubility of the protein harvested from bacterial and insect host cells; and (vii) selecting a host cell or production condition based on results of the comparing step.

This application refers to various patents and publications. The contents of all of these are incorporated by reference. In addition, the following publications are incorporated herein by reference: *Baculovirus Expression Protocols* (Methods in Molecular Biology Vol 39), Christopher Richardson, (ed.), Humana Press, 1998; *Baculovirus Expression Vectors: A Laboratory Manual*, Miller, L, Lucknow, V. A., O'Reilly, D. R., Oxford University Press, 1997; *Current Protocols in Molecular Biology, Current Protocols in Immunology, Current Protocols in Protein Science, Current Protocols in Cell Biology*, all John Wiley & Sons, N.Y., edition as of July 2002; Sambrook, Russell, and Sambrook, *Molecular Cloning: A Laboratory Manual*, 3$^{rd}$ ed., Cold Spring Harbor Laboratory Press, Cold Spring Harbor, 2001.

BRIEF DESCRIPTION OF THE DRAWING

FIG. 1A is a schematic map of the pBEV expression vector. The vector contains: polh: T7lac promoter regions, multiple cloning site (MCS), flanking *Autographa californica* nuclear polyhedrosis viral (AcNPV) region for recombination, the ColE1 origin of replication derived from the high copy number cloning vector pUC, the M13 origin for preparation of single strand DNA for mutagenesis and the β-lactamase gene for selection.

FIG. 1B (SEQ ID NO: 1) shows and describes the sequence of a hybrid polh: T7lac promoter region, with the continuous lines identifying the polh promoter, T7lac promoter and operator regions. The putative and actual ribosomal binding sites of polh and T7lac promoter, TAAG and AGGAG respectively, are underlined. Dotted line indicates the 5' untranslated portion of the polh mRNA transcript. The distance from the site of the original polh ATG to the new ATG start codon (in bold) is indicated. The x indicates the first nucleotide of a minimal polh promoter.

FIG. 1C shows the complete nucleotide sequence of pBEV (SEQ ID NO: 2).

FIG. 1D shows an example of a hybrid promoter region (SEQ ID NO: 3) that includes a minimal polh promoter together with the polh 5' UTR located upstream of the T7 lacO promoter and an RBS.

FIG. 1E shows an example of a minimal polh promoter (SEQ ID NO: 4).

FIG. 3A shows growth-curves of *E. coli* cells in a shake-flask and in a deep-well block. A dotted line and a continuous line represent growth in shake-flasks and deep-well blocks, respectively.

FIG. 3B shows growth-curves of insect cells in a shake-flask and in a deep-well block. A dotted line and a continuous line represent growth in shake-flasks and deep-well blocks, respectively.

DEFINITIONS

Figure 2:
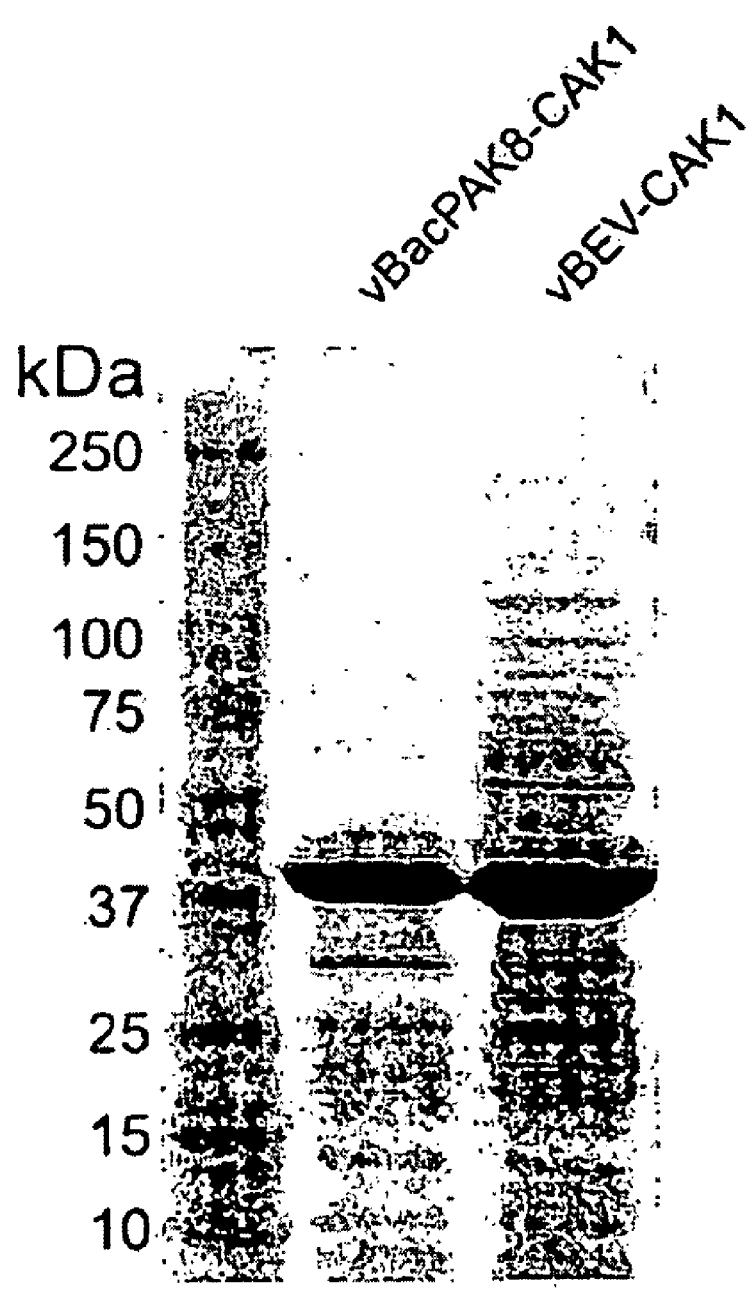
FIG. 2 shows an SDS-PAGE analysis of comparative expression and purification of CAK1 expressed using vBEV and vBacPAK8, indicating equivalent production between the two systems.

Operably linked: As used herein, "operably linked" refers to a relationship between two nucleic acid sequences wherein the expression of one of the nucleic acid sequences is controlled by, regulated by, modulated by, etc., the other nucleic acid sequence. For example, the transcription of a nucleic acid sequence is directed by an operably linked promoter sequence; post-transcriptional processing of a nucleic acid is directed by an operably linked processing sequence; the translation of a nucleic acid sequence is directed by an operably linked translational regulatory sequence; the transport or localization of a nucleic acid or polypeptide is directed by an operably linked transport or localization sequence; and the post-translational processing of a polypeptide is directed by an operably linked processing sequence. Preferably a nucleic acid sequence that is operably linked to a second nucleic acid sequence is covalently linked, either directly or indirectly, to such a sequence, although any effective three-dimensional association is acceptable.

Purified: As used herein, "purified" means separated from one or more other compounds or entities, e.g., entities with which it is otherwise found. A compound or entity may be partially purified, substantially purified, or pure, where it is pure when it is removed from substantially all other compounds or entities, i.e., is preferably at least about 90%, more preferably at least about 91%, 92%, 93%, 94%, 95%, 96%, 97%, 98%, 99%, or greater than 99% pure. For example, when a protein is expressed in a cell, it will be considered purified when it is removed from one or more, preferably most, other cellular components, such as other proteins expressed by the cell.

DETAILED DESCRIPTION OF CERTAIN PREFERRED EMBODIMENTS OF THE INVENTION

The ever-expanding amount of sequence information, including the sequence of the entire human genome, has led to an increasing need for efficient protein production systems to facilitate characterization of the proteome. Expressed proteins are used, for example, in biochemical and enzymatic studies as well as for crystallization and structure determination. In addition, the increasing development of protein based therapeutics indicates that testing of variants of naturally occurring proteins, e.g., to identify altered forms with improved properties, will grow in importance. These factors, among others, have motivated the development of efficient systems and methods for expressing proteins in host cells.

The inventors have recognized that an important determinant in developing an appropriate expression system for a protein of interest is the selection of an appropriate host cell. For example, bacterial hosts such as *E. coli* offer a number of advantages such as high expression levels, ease in culturing large volumes of cells, low cost, etc. However, certain proteins are either poorly expressed in bacteria, insoluble, or, in the case of proteins from eukaryotic organisms, lack post-translational processing that is needed for activity, etc. In general, the factors that make one or another cell type most suitable for production of a protein of interest are not clear prior to actually producing the protein in different host cells and performing appropriate purification and/or testing.

The inventors have recognized that in order to efficiently express multiple proteins and to select appropriate host cells it would be desirable to culture cells in small volumes, e.g., in multiple well vessels, rather than in individual shake flasks. Using small volumes and multiple well vessels allows for automation, reduces cost, and increases throughput. Once appropriate host cells have been selected, the process can be scaled up for production of larger quantities. However, addition to selection of host cell, the size of the culture volume can affect variables such as expression level, solubility, etc. Thus in order to provide a means of testing in small volumes that can reliably predict results when cultures are scaled up, it is important to have promoters, vectors, and culture and purification methods whose performance is approximately equal in small and large volumes.

The present invention provides a dual expression vector that contains a dual promoter cassette including first and second promoters that support gene expression in both prokaryotic (bacterial) cells such as *Escherichia coli* (*E. coli*) and in insect cells, two of the most common hosts used for production of recombinant proteins. Thus the vector contains a promoter effective for expression of a downstream coding sequence in bacterial cells and a promoter effective for expression of a downstream coding sequence in insect cells, e.g., insect cells that express baculovirus proteins such as insect cells that have been infected with a baculovirus or that harbor baculovirus genes within their genome. A user can insert a polynucleotide that encodes a protein of interest at any of a number of locations downstream of (i.e., 3' from) the promoters. The resulting vector can then be introduced into bacterial host cells, which then express the protein of interest. Preferred vectors can also be used for the production of recombinant baculovirus using standard techniques. The resulting baculovirus derived from the vector includes the dual promoter and coding sequence within its genome. The baculovirus is introduced into insect cells (e.g., by infection), which then results in expression of the protein of interest. The invention further provides expression systems comprising any of the various inventive vectors and an appropriate host cell or host cells.

The bacterial or insect host cells can be cultured under standard conditions used for protein production, e.g., in vessels such as shake flasks, typically in volumes of at least 50-100 ml, or greater, e.g., 500 ml, 800 ml, 1 liter, etc. Alternately, the bacterial or insect host cells can be cultured in small volumes, e.g., less than or equal to 10 ml, less than or equal to 5 ml, or less than or equal to 2 ml. For example, the host cells can be cultured in deep well blocks as described in Examples 3-5. For purposes of the present invention a culture volume of greater than 50 ml will be referred to as a large scale culture volume while a culture volume of less than 10 ml will be referred to as small scale culture volume. One feature of certain preferred vectors described herein is that the promoters and expression systems function approximately equally effectively in large scale culture volumes and small scale culture volumes. For example, according to certain preferred embodiments of the invention protein production using the vectors of the invention in a small scale system is within 50% of protein production when the vectors are used in a conventional large scale system.

FIG. 1A shows an example of a preferred embodiment of a dual expression vector. This vector contains a region, referred to as a hybrid promoter region on the figure, that includes a promoter effective to express a protein of interest in insect cells, e.g., insect cells that express baculovirus proteins, and also contains a promoter effective to express a protein of interest in bacterial cells. The arrows show the direction of transcription and also indicate the 5' to 3' direction on the vector.

Preferred inventive vectors also contain baculovirus sequences, indicated as AcNPV, that enable production of recombinant baculovirus using the vector, using standard methods (see Examples for further details). The vector also contains an origin of replication that supports replication in bacterial cells. A ColE1 origin is depicted, but any of a number of other origins of replication, such as those present on various different plasmids, could be used. Numerous origins of replication are known in the art [37]. The origin of replication can be a high copy number origin (such as that found within pUC-based plasmids) or a medium or low copy number origin (such as that found in plasmids based on pBR322). A eukaryotic origin of replication, e.g., a yeast autonomously replicating sequence (ARS), or a sequence that supports episomal replication in mammalian cells, could also be included.

Additional vector features preferably include a selectable marker (e.g., the ampicillin resistance gene). Any of a wide variety of selectable markers known in the art could be used, e.g., chloramphenicol, kanamycin, or tetracycline resistance markers for use in bacteria. Selectable markers for use in various eukaryotic host cells include, for example, the neo gene, puramycin resistance gene, zeomycin resistance gene, etc. An optional M13 origin is also present, which can be used for production of single stranded DNA, e.g., for sequencing. A multiple cloning site (MCS), may be included downstream of the hybrid promoter region, but is not necessary. In general, at least one cloning site such as a restriction site is present downstream of the promoter region. As described below, the inventive vectors include a cloning site into which a polynucleotide of interest can be inserted. Certain vectors of the invention include one or more transcription termination signals located downstream of the cloning site. For example, a transcription termination sequence effective in bacterial cells and/or a transcription termination sequence effective in insect cells is included in certain embodiments. Such sequences are well known in the art. A polynucleotide to be inserted into the vector may also include such a site.

FIG. 1B shows and expanded view of the sequence of the hybrid promoter portion of an exemplary vector of the invention. The portion includes a promoter that supports expression in insect cells. Preferably a baculovirus promoter, e.g., a late or very late promoter such as the polh promoter (shown) or p10 promoter is used. Such promoters support high levels of expression of downstream genes in cells that express baculovirus proteins, e.g., cells infected with baculovirus. Where a polh promoter is used, the region downstream of the promoter preferably includes at least a portion of the 5' untranslated region (UTR) that is found in naturally occurring polh mRNA transcripts.

The asterisk (*) in FIG. 1B indicates the first nucleotide (A) of the polh 5' UTR. The underlined sequence TAAG represents the putative site that is recognized by RNA polymerase to begin transcription, and is preferably included in the vectors that include the polh promoter to provide efficient transcription in insect cells though the sequence could be varied. Thus in the vector shown in FIG. 1B, transcription in insect cells begins with the A indicated by an asterisk, and contains an untranslated region upstream of the translation start site. This untranslated region includes the second promoter (discussed below) and additional sequences that are not found in the context in which the polh promoter naturally occurs. However, as demonstrated in the Examples, it has been found that the presence of these additional sequences does not have a deleterious effect upon expression, relative to expression vectors in which these additional sequences are absent. In addition, contrary to certain prior art teachings, it has been found that high level expression from the polh promoter does not require a 5' portion of the sequence encoding Polh. Unlike a number of other expression vectors that make use of the polh promoter, certain of the inventive vectors such as that including the portion shown in FIG. 1B do not include the codons that encode an N-terminal portion of Polh immediately 3' of the polh mRNA 5' UTR. Instead, the second promoter sequence begins immediately following the UTR, thus providing a compact dual promoter region. For example, the construction of the pVL series of vectors by Luknow and Summers (39), which have subsequently become the vector of choice for expression in insect cells, mutated out the natural ATG site and had the effect of moving the ATG start codon 30-40 nucleotides downstream of its original location in the polh gene, thus retaining polh coding sequence upstream of the start site of an inserted polynucleotide encoding a protein of interest [38, 39]. The experimental data presented herein shows that there appears to be no detrimental affect on expression, resulting from removing sequences downstream from the natural polh ATG site, contrary to previous reports. The inventors have taken advantage of this finding to insert a second promoter for expression in bacterial host cells, resulting in a compact dual promoter region, as discussed below.

It is not necessary that the vector include the entire 5' portion of the sequence shown in FIG. 1B. In particular, sequences 5' of the nucleotide indicated with an "x" may be omitted in certain embodiments of the invention since the minimal polh promoter is believed to begin at this nucleotide and extend in a 3' direction from it. Thus in certain embodiments of the invention the promoter for expression in insect cells comprises the sequence presented in SEQ ID NO: 4.

As indicated in FIG. 1B, the hybrid promoter region also contains a bacterial promoter (i.e., a promoter effective to express a protein of interest in bacteria) downstream of the promoter for insect cell expression. The promoter can be constitutive (i.e., active in the absence of a specific inducer or inducing condition), inducible (i.e., inactive in the absence of a specific inducer such as a small organic molecule, metal, or an environmental condition such as elevated temperature, etc). A T7 promoter is shown, which is inducible upon the addition of IPTG to culture medium, but any of a number of other promoters such as other phage promoters (e.g., pL, etc.) could be used. Other suitable bacterial promoters include Lac, Trp, Tac, and pBAD. It will be appreciated that where a phage promoter such as the T7 promoter is used, the appropriate RNA polymerase (e.g., T7 RNA polymerase) should be expressed within the host cell. A sequence encoding the polymerase operably linked to a promoter is preferably provided by the host cell genome (many such bacterial hosts are known in the art) but can alternatively be included on an inventive vector, or provided by a different vector present in the host cell.

An operator sequence, e.g., the lac operator, can be included, to allow repression of the bacterial promoter. For example, the configuration shown in FIG. 1B includes a T7 promoter and a downstream Lac operator (i.e., a site for binding of the lac repressor), forming a well-known unit found in many standard prokaryotic expression vectors and commonly referred to as the T7 lac or T7 (lacO) promoter. The T7 and lac operator sequences are indicated with solid arrows above the sequence. In general, the presence of (lacO) following a promoter name herein is taken to indicate that the promoter unit includes a lacO operator. The lacO operator represses transcription of the promoter in the presence of the lac repressor, which is useful, for example, to reduce basal expression levels in a bacterial host cell. In general, the lac repressor can be encoded by a transcription unit present within a vector of the invention or can be expressed by the host cell either from the host cell genome or from another vector. Other operators could also be used. Alternate methods of reducing basal expression include use of host cells that express an inhibitor of T7 RNA polymerase, e.g., T7 lysozyme.

Translation in bacterial host cells usually begins at a start codon (ATG) in the mRNA, located approximately 5-10 nucleotides downstream of a sequence referred to as a Shine-Dalgarno sequence or ribosome binding site. The inventive vectors preferably include such a ribosome binding site (RBS) downstream of the bacterial promoter or promoter/operator portion. A consensus sequence for an effective ribosome binding site is AGGAGG, but many variants including both shorter and longer sequences exist that support efficient translation. Typically these sequences are AG rich. For example, a sequence such as AGGA, AGGAG, etc., could be used. The ribosome binding site AGGA is underlined in FIG. 1B. The sequence shown in FIG. 1B includes additional sequence elements located between the 3' end of the lac operator and the ribosome binding site (a 32 nucleotide sequence). These sequences have been previously found to be helpful for efficient transcription from the T7 and T7lac promoters and from other bacterial promoters. Accordingly, some or all of this region is preferably included in certain of the vectors of the invention.

In certain preferred inventive vectors the promoter for expression in bacterial host cells is located between the promoter for expression in insect cells and the start site of a sequence encoding a protein of interest, as shown in FIG. 1B. This configuration allows the bacterial promoter to be positioned close to the start site and avoids the need to include the promoter for expression in insect cells between the bacterial promoter and the translation start site. For example, this configuration allows the well-characterized T7lac promoter region to remain intact and at a distance from the RBS and translation start site that is known to result in efficient expression. This reduces the possibility that RNA secondary structures may form, which can reduce expression and allows maintenance of preferred spacing between bacterial promoter and RBS elements. This feature contrast with certain other vectors (see, e.g., reference 2 and U.S. Pat. No. 6,589,783), in which such spacing is not retained. Thus in certain preferred vectors the distance between the end of the bacterial promoter (or, where present, the operator), and the RBS is less than or equal to 100 nucleotides, less than or equal to 50 nucleotides, or approximately 30 nucleotides, or between approximately 30 and 100 nucleotides. For example, in the sequence shown in FIG. 1B, the distance between the end of the lac operator and the first nucleotide of the RBS is 32 nucleotides, including both terminal nucleotides. Certain vectors of the invention comprise a portion having the sequence of SEQ ID NO: 3, which includes a minimal polh promoter together with the polh 5' UTR, upstream of the T7 lacO promoter. The sequence also includes an RBS. The sequence may be directly followed by a start codon (ATG). If the sequence is directly followed by ATGG, then an NcoI site is created, which is convenient for cloning purposes. Thus the invention includes vectors comprising SEQ ID NO: 3, to which A, ATG, or ATGG is appended in the 3' direction. In certain embodiments of the invention the distance between the 5' end of the promoter for expression in insect cells and the 3' end of the RBS, encompassing a minimal promoter for expression in insect cells, a bacterial promoter, an RBS, and optionally an operator, is less than 200 nucleotides (see, e.g., FIG. 1E). In certain embodiments of the invention the region extending from the 5' end of a minimal promoter for expression in insect cells to the 3' end of a promoter for expression in bacteria is less than 110 nucleotides.

The vectors of the invention include a cloning site for insertion of a polynucleotide of interest (e.g., a polynucleotide that encodes a protein of interest) downstream of the two promoters, and downstream of the RBS. In general, any restriction enzyme site may serve this purpose. In the example shown in FIG. 1B, the sequence CCATGG, encompassing the ATG start codon shown in bold, is an NcoI site. A polynucleotide of interest can be inserted at this site using standard techniques, preferably reconstructing the ATG. Alternately, a polynucleotide of interest can be inserted at the indicated NdeI, XhoI, or BamH1 sites or between any two of these sites. The vector can also include different sites or additional sites. For example, certain embodiments include a multiple cloning site, or polylinker, downstream of the RBS. A dual promoter cassette including the polh promoter, bacterial promoter, and RBS shown in FIG. 1B can be inserted into any of a variety of different vector backbones to produce a family of vectors with desired features, e.g., different tags, resistance markers, etc.

As shown in FIG. 1B, various vectors of the invention include an optional sequence encoding a tag, so that insertion of a polynucleotide encoding a protein of interest results in production of a fusion protein having an N-terminal or C-terminal tags. Such tags can be used, for example, for detection (e.g., by Western blot) and/or purification of the fusion protein. For example, if a polynucleotide encoding a protein of interest is inserted into the NdeI, XhoI, or BamHI site or between any two of these, the resulting protein will include an N-terminal 6X-His tag. This tag allows for purification using commercially available histidine binding resins (see Examples) and also allows detection using commercially available antibodies. Other epitope tags that could be used include influenza hemagglutinin (HA), Myc, Flag, glutathione-S-transferase (GST), maltose binding protein (MBP), etc. A sequence encoding a protease cleavage site can also be included so that the tag can be cleaved off the protein, e.g., after using it for purification. Versions with multiple tags are also encompassed. Such tags can be at either the 5' or 3' end of an expressed fusion protein, depending upon the position of the sequence(s) encoding the tag(s) relative to the position at which a polynucleotide encoding the protein of interest is inserted. It will be appreciated that attention must be paid to maintaining an appropriate reading frame so that the tag will be translated properly, which can readily be accomplished, e.g., by appropriate primer selection.

The vectors can be introduced into bacterial host cells using standard methods, e.g., electroporation, transformation, etc. Any of a wide variety of hosts can be used. In certain embodiments of the invention a protease deficient host is preferred.

The vectors can be used for production of recombinant baculovirus using methods well known in the art. These methods generally take advantage of homologous recombination between baculovirus sequences present in the vectors and baculovirus DNA. Various insect cells have been grown in culture and any of these cells can be transformed with the recombinant expression vectors of this invention. Such cultured insect cells include *Spodoptera frugiperda* cells lines Sf9 (ATCC accession # CRL 1711) and Sf21, *Bombyx mori, Heliothis zea, Trichoplusia ni* (High-5 cells), *Manduca sexta, Malacosoma disstria, Lymantria dispar* (Ld652Y cells) and *Drosophila Schneider* (S2 cells) cells. Recombinant baculovirus can be produced by co-transfection of the vector with linearized *Autographa californica* nuclear polyhedrosis virus (AcMNP) baculovirus DNA into cells (e.g., Sf9 cells) using Lipofectin™ transfection agent (Gibco-BRL) or other appropriate reagents. The recombinant virus is then used to infect insect cells, e.g., Sf9, Sf21, High-5, etc.

As is known in the art, baculoviruses are known to efficiently transduce vertebrate cells, such as mammalian cells, and express proteins of interest under the control of vertebrate promoters (2, and references 11-13 therein). Thus by adding a third promoter, e.g., a mammalian promoter or promoter/enhancer, such as those mentioned in (2) or other promoters suitable for expression in vertebrates such as mammals, the host cell range can be expanded. The third promoter or promoter/enhancer is located upstream of the promoter effective for expression in bacterial cells, and preferably also upstream of the promoter effective for expression in insect cells. Suitable promoters include SV40, viral long terminal repeat (LTR), EF1α, constitutive promoters such as actin or tubulin promoters, inducible promoters such as steroid-responsive promoters, metal-responsive promoters (e.g., metallothionine promoter), etc. It is noted that unless otherwise indicated, the terms "first promoter", "second promoter", and "third promoter" do not necessarily indicate the 5' to 3' order of the promoters in a vector.

Mammalian promoters and promoter/enhancer elements have been shown to effectively support expression of downstream coding sequences even when located a considerable distance from the start codon and even where the sequence between the promoter and the start codon includes sequences such as insect and bacterial promoter sequences that are not normally found in this context. Thus the presence of a long heterologous 5' UTR is not incompatible with efficient expression from mammalian promoters. Preferably the vector includes a Kozak consensus sequence upstream of the start codon for efficient translation in mammalian cells.

The host cell range be similarly expanded to include fungal cells by including a fungal promoter as the third promoter. Plant promoters such as the cauliflower mosaic virus (CMV) promoter could also be used to further expand the host range. It is noted that although use of baculovirus promoters is preferred, promoters from various insect cell genes could also be used instead. In addition, baculovirus promoters other than the late/very late promoters mentioned herein could be used, although expression levels are generally higher with the late/very late promoters. However, in certain situations it may be desirable to limit the amount of protein produced, e.g., in the case of a protein that is deleterious to the host cell.

Host cells into which a recombinant vector containing a polynucleotide, e.g., a polynucleotide encoding a protein of interest inserted into the cloning site, or host cells containing a recombinant baculovirus derived from such a vector has been introduced can be cultured under various different culture conditions. The Examples describe both standard culture conditions, e.g., in shake flasks, and a culture system in which cells are grown in small volumes in a multi-well vessel, in this case a deep well block. The latter system is useful for high throughput screening of different host cells and proteins. For example, it is useful to culture bacterial and host cells, both expressing a protein of interest using either a an expression vector or baculovirus of the invention, in parallel. After a growth period, cells are harvested. A cell lysate is then prepared and tested to determine, for example, the amount of protein produced and its solubility. The protein may be purified or partially purified using various techniques such as those described in the Examples or otherwise known in the art. Results obtained using different host cells can be compared, and an appropriate host cell identified. Multiple different host cells can be tested. For example, multiple different bacterial strains and/or insect cell lines can be tested. In addition, multiple different production conditions can also be tested in parallel. For example, different culture media can be used.

Figure 8:
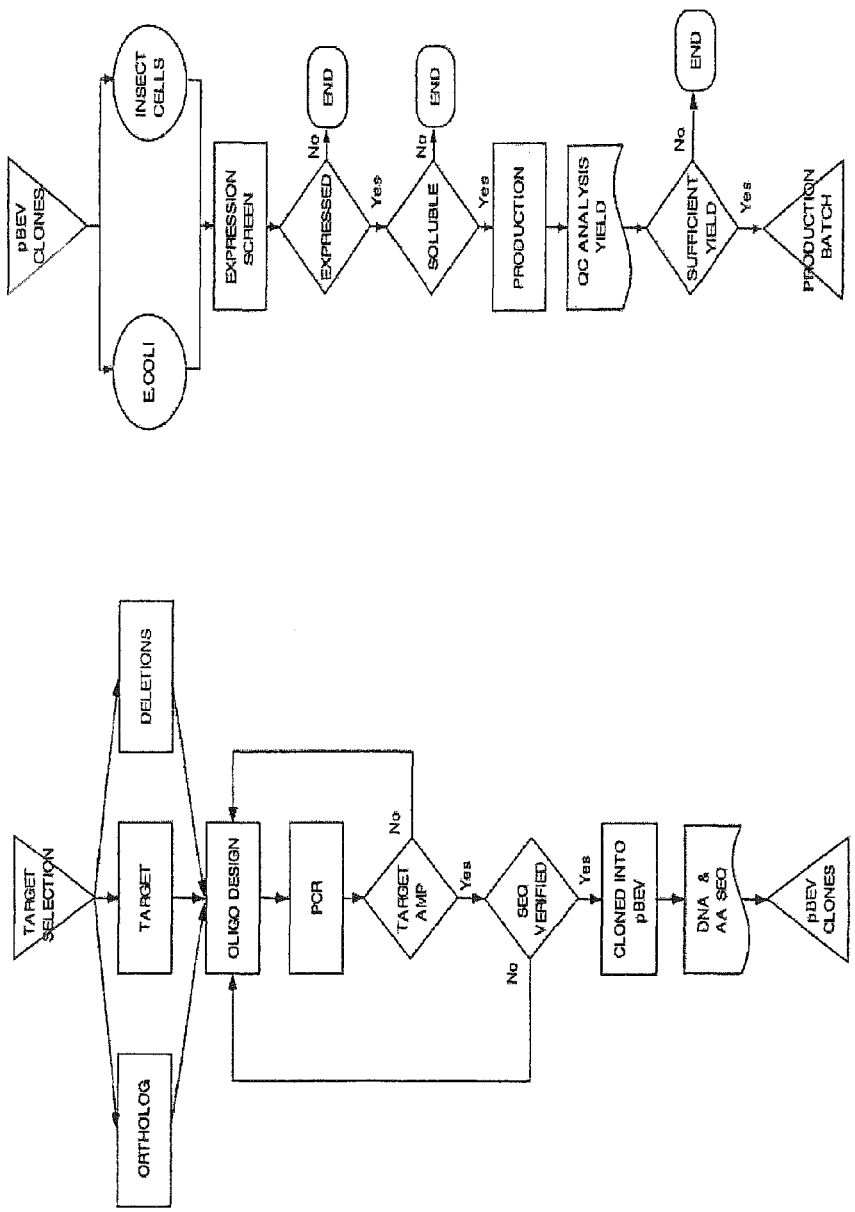
FIG. 8 presents a schematic high throughput cloning and expression process utilizing the vectors of the invention.

FIG. 8 presents a schematic diagram of a high throughput cloning and expression process in accordance with the present invention. A polynucleotide of interest is obtained, e.g., using PCR, and is cloned into a vector of the invention (e.g., pBEV), as shown in the left portion of the figure. Sequence verified clones are used for expression in insect cells and bacteria, and the resulting host cells are screened in parallel for protein production. Proteins that are expressed and soluble in either system are further analyzed, and production can then be scaled up.

As described in the Examples, certain vectors of the invention have been used for production of numerous different proteins, and it has been found that the expression levels achieved are comparable to those achieved using single promoter expression vectors. In addition, the small scale culture results indicate that the vectors perform comparably in small and large culture volumes, and that automated purification of proteins from small culture volumes replicates findings using conventional purification schemes. Thus the invention provides a high throughput screening platform for the production of proteins in host cells. It is noted that inventive vectors can be conveniently tested by inserting a polynucleotide encoding a reporter protein into the cloning site and assessing expression of the reporter. Numerous suitable reporters are known in the art including, for example, fluorescent proteins such as green fluorescent protein (GFP) and variants thereof, luciferase, enzymes such as β-galactosidase, etc.

Any of the vectors described herein may be provided in the form of a kit, which allows the user to conveniently insert a polynucleotide, e.g., a polynucleotide encoding a protein of interest, into the vector and express the polynucleotide. In addition to one or more vectors, such a kit may include any of the following items: bacterial host cells, insect host cells, baculovirus DNA, transfection reagent, agarose, an inducer, a restriction enzyme, a ligation mix, culture medium, an antibody, a buffer, a control plasmid, and instructions for use.

EXAMPLES

Example 1

Construction of Expression Vectors and Recombinant Baculoviruses

The expression vector pBEV was constructed from a commercially available vector pBacPAK8 (BD Biosciences-Clontech, Palo Alto, Calif., USA) by inserting a 155 by BglII-BamHI fragment, isolated from pET15b (Novagen, Madison, Wis., USA) into the BamHI site of pBacPAK8. This fragment contains the T7lac promoter (the T7 promoter and lac operator sequences), a thrombin-cleavable His-tag sequence, and a portion of the polylinker. The polh promoter from pBacPAK8, now in series with the inserted T7lac promoter, was optimized for expression by removal of a portion of the sequence upstream of the T7lac promoter, reducing the distance between the polh start codon at position +1 and the ATG start codon to 86 bases. The resulting sequence of tandem promoters is a common feature present in all the pBEV family of vectors, described herein (FIG. 1).

The pBEV vectors contain the high copy number origin of pBacPAK8, derived from pUC18, in pBEV rather than the low copy number origin of replication of pET15b, derived from pBR322. Including this origin increases the gene dosage and resultant recombinant protein expression in *E. coli* [15].

FIG. 1A shows a schematic map of the pBEV expression vector. The vector contains: polh: T7lac promoter regions, multiple cloning site (MCS), flanking *Autographa californica* nuclear polyhedrosis viral (AcNPV) region for recombination, the ColE1 origin of replication derived from the high copy number cloning vector pUC, the M13 origin for preparation of single strand DNA for mutagenesis, and the β-lactamase gene for selection.

FIG. 1B shows and describes the sequence of the hybrid polh: T7lac promoter, with the continuous lines identifying the polh promoter, T7lac promoter and operator regions. The putative and actual ribosomal binding sites of polh and T7lac promoter, TAAG and AGGAG respectively, are underlined. Dotted line indicates the 5'-mRNA untranslated polh transcript. The distance from the site of the original polh ATG and the new ATG start codon (in bold) is indicated.

FIG. 1C shows the complete nucleotide sequence of pBEV1.

pBEV, unlike pET15b, does not contain the lac repressor gene in its backbone. This feature coupled with increased copy number, results in less stringent regulation of its T7lac promoter. Basal expression in *E. coli*, directed by the T7lac promoter, was minimized by using *E. coli* containing pLysS, resulting in expression of T7 lysozyme, a natural inhibitor of T7 RNA polymerase [16]. All *E. coli* expression described in the following Examples was performed in BL21 [F−, ompT, hsdS$_B$ (r$_B^-$, m$_B^-$) gal, dcm] (DE3) pLysS, which provides a protease deficient background for the expression of protease sensitive proteins [17].

To construct a pBEV 1-based vector for expression of a protein of interest, an open reading frame encoding full length cyclin activating kinase (CAK1) isolated from *Candida albicans* [25] was cloned into pBEV1 to generate pBEV-CAK1. The same open reading frame was also cloned into pBacPAK8 to generate pBacPAK-CAK1. pBEV-CAK1 and pBacPAK-CAK1 were co-transfected with linear *Autographa californica* nuclear polyhedrosis viral (AcNPV) DNA into *Spodoptera frugiperda* (Sf9) insect cells to generate the baculovirus recombinants vBEV-CAK1 and vBacPAK-CAK1 using lipofectin transfection agent (Gibco-BRL). Individual recombinant baculovirus clones were purified by plaque assay, amplified to a high titer ready to infect insect cells.

Example 2

Comparison of Dual Promoter with Single Promoters

A comparison of the performance of the polh:T7 lac promoter in pBEV with its progenitor, the polh promoter in pBacPAK8 was undertaken. *Trichoplusia ni* insect cells (High-5 cells), were grown in suspension in Excell-405 protein free media in a shake flask at 110 revolutions per minute (rpm) at 27° C. Cells at a density of $2\times10^6$ cells/ml were infected with recombinant baculovirus vBEV-CAK1 or vBacPAK8-CAK at a multiplicity of infection (moi) of 2.5. Cells were subsequently harvested at 72 hours post-infection when cell viability was within the 70-80% range. Cell pellets or media were flash frozen at −70° C. until ready for purification.

The analysis of protein expression from large-scale protein production was performed on 500 mg of the cell pellet resuspended in 10 ml of lysis buffer, chilled and sonicated using with a micro-tip probe (Misonix Inc., Framingdale, N.Y., USA) with a single 0.5 min pulse. Following centrifugation at 30,000 g for 30 min, the supernatant was added directly to 350 ul of pre-equilibrated Ni-NTA resin, batch incubated for 2 h at 4 C, and washed with 100-fold column volume with lysis buffer. His-tagged protein was then eluted from the column using 5×150 l of lysis buffer with 200 mM imidazole. The proteins were analyzed following isolation by SDS-PAGE and stained with Coomassie Blue.

The results of side-by-side expression and purification of CAK1 are shown in FIG. 2. Under identical conditions for expression and purification, similar levels of CAK1 were produced in insect cells using vBEV-CAK1 and vBacPAK8-CAK1, with the level using vBEV-CAK1 if anything higher than that using vBacPAK8-CAK1. These results demonstrate that the addition of the T7 promoter region in the polh: T7lac promoter of pBEV is not deleterious to polh promoter directed expression in insect cells.

Similar results were obtained in *E. coli*. A coding sequence for PTP1b (protein tyrosine phosphatase 1b) was inserted into pBEV between the NdeI and BamH1 sites to generate pBEV-PTP1b. A comparison between expression in *E. coli* achieved using the standard *E. coli* expression vector pET15 to express from the T7lac promoter and expression using pBEV-PTP1b showed that the dual promoter containing the polh promoter upstream of the T7lac promoter performs equally well as a T7lac promoter in a standard context for expression in *E. coli*.

Example 3

Comparison of Cell Growth in Shake Flasks and Deep Well Blocks

To compare cell growth of *E. coli* in deep well blocks with standard growth conditions in shake flasks, *E. coli* BL21 (DE3) pLysS was placed in a 24-well block (5 ml culture volume), aseptically sealed with AirPore™ tape sheets (Qiagen, Valencia, Calif., USA) and grown using a HiGro™ incubator-shaker (Gene Machines, San Carlos, Calif., USA) at 37° C. for 4.5 h in Brain Heart Infusion (BHI) media (Becton Dickinson & Company, Sparks, Md., USA) supplemented with 100 µg/ml carbenicillin and 35 µg/ml chloramphenicol.). The 5 ml cultures growing in a 24-well block were sampled every hour and absorbance ($A_{600nm}$) recorded. *E. coli* were also cultured in a 2 liter Shake flask under standard conditions in the same medium, and samples were periodically removed for measurement of absorbance ($A_{600nm}$). Over the time period sampled cell densities of the 24-well block were found to be comparable to an 800 ml culture grown in a 2 liter Shake flask. FIG. 3A shows growth-curves of *E. coli* in a shake-flask and in a deep-well block. A dotted line and a continuous line represent growth in the shake-flask and in the deep-well block, respectively.

*Trichoplusia ni* insect cells (High-5 cells) were grown in suspension in Excell-405 protein free media in a Shake shake flask at 110 revolutions per minute (rpm) at 27° C. Cells at a density of $2\times10^6$ cells/ml were infected with recombinant baculovirus generated from pBEV-based vectors at a multiplicity of infection (moi) of 2.5 and samples were periodically removed for measurement of absorbance ($A_{600nm}$).

High-5 insect cells were grown to a density of $2.0\times10^6$ cells/ml in a shake flask. Insect cell expression in a 24-well block was initiated by infecting 2.5 ml of the afore-mentioned cells at a multiplicity of infection (MOI) of 5 pfu/cell with recombinant baculovirus generated from pBEV-based vectors were grown in deep well blocks for 72 h at 28° C. in serum-free EX-CELL™ 405 media with L-glutamine (JRH Biosciences, Lenxa, Kans., USA). The 3 ml culture grown in a 24-well block was sampled every 12 h and the number of viable cells determined (FIG. 3B) using a Cedex analysis system (Innovatis GmbH, Bielefeld, Germany). Viabilities obtained from cells grown in the HiGro™ incubator-shaker appeared comparable to those obtained from cultures grown in a Shake flask. FIG. 3B shows growth-curves of insect cells in a shake-flask and in a deep-well block. A dotted line and a continuous line represent growth in the shake-flask and in the deep-well block, respectively. It is noteworthy that the rate of infection also appears better in the 24-well block than in the flask, possibly due to the higher vortex action in the 24-well block produced by the HiGro™ incubator-shaker.

Example 4

Comparison of Protein Expression in Shake Flasks and Deep Well Blocks

To validate use of the system for purposes such as high throughput screening in a small volume, it was established that expression with pBEV could be reduced in volume while still providing results that replicated those seen at larger volumes. This was achieved by analyzing recombinant proteins produced in *E. coli*, purified from 5 ml volume of cultures grown in a 24-well block with proteins produced in *E. coli* cultured in a Shake flask (5 ml from a 1 liter culture) and by analyzing recombinant proteins produced in High5 insect cells cultured either in a 24-well block or in a Shake flask (2 ml from an 800 ml culture).

Coding sequences for full length extracellular signal-regulated kinase 2 (ERK-2) and mitogen-activated protein kinase p38α (P38) were inserted into pBEV between the NdeI and BamH1 sites, resulting in expression vectors pBEV-ERK2 and pBEV-P38. These vectors were transformed into *E. coli* BL21 (DE3) pLysS. Transformants were grown overnight at 37° C. in 5 ml BHI medium in a 24-well block. Overnight cultures were pelleted at 2,000 g for 5 min using a micro-titer plate centrifuge and re-suspended in 1 ml BHI media. 5 ml of fresh BHI media was inoculated with 20 µl of re-suspended overnight culture and grow at 37° C. for 3-4 h in the 24-well block. Expression was induced at mid-log phase ($A_{600nm} \approx 1$) with the addition of 1 mM isopropyl-β-D-thiogalactopyranoside (IPTG). Cells were harvested 6-8 h after induction by centrifugation at 2,000 g for 5 min.

Coding sequences for truncated T-cell specific kinase (TSK: G354-L620) and With No K (lysine)-1 (WNK1: P180-G602) were inserted into pBEV between the NdeI and BamH1 sites, resulting in expression vectors pBEV-TSK and pBEV-WNK1. These vectors were co-transfected with linear *Autographa californica* nuclear polyhedrosis viral (AcNPV) DNA into *Spodoptera frugiperda* (Sf9) insect cells to generate the baculovirus recombinants vBEV-TSK and vBacPAK- WNK1. High-5 insect cells used for expression were grown to a density of 2.0×10⁶ cells/ml in a Shake flask. Insect cell expression in a 24-well block was then initiated by infecting 2.5 ml of the aforementioned cells with high-titer baculovirus at an MOI of 5 pfu/cell. Cells were then grown in serum-free EX-CELL™ 405 with L-glutamine at 27° C. for 48-60 h following infection and harvested at 70-80% viability by centrifugation at 2,000 g for 5 min.

For comparison with expression in 24-well blocks, proteins expressed in insect cells using recombinant baculoviruses were purified from 2 ml volume of cultures infected in a Shake flask (2 ml from a 800 ml culture). *Trichoplusia ni* insect cells (High-5 cells) were grown in suspension in Excell-405 protein free media in a Shake shake flask at 110 revolutions per minute (rpm) at 27° C. Cells at a density of 2×10⁶ cells/ml were infected with recombinant baculovirus vBEV-TSK and vBacPAK-WNK1 at a multiplicity of infection (moi) of 2.5. Cells were subsequently harvested after 72 hours post-infection when cell viability was within the 70-80% range. Cell pellets were flash frozen at −70° C. until ready for purification.

Purification of proteins from cells grown in 24-well blocks was carried out with nickel-nitrilotriacetic acid (Ni-NTA) magnetic agarose beads (5% suspension) using the BioRobot 3000 automated liquid handling system (Qiagen, Valencia, Calif., USA). A protocol adapted from the manufacturer's manual was used for the purification of cultures grown in the 24-well blocks. Following expression the cell pellets were re-suspended in 400 μl lysis buffer; 10 mM Tris-HCL (pH 8.0), 50 mM $NaH_2PO_4$, 100 mM NaCl, 20% glycerol, 0.25% Tween-20 and 10 mM imidazole. Lysis in the presence of 0.1% benzonase solution (Novagen, Madison, Wis., USA) was performed using a deep-well cup horn sonicator (4×1 min bursts) (Misonix Inc., Farmingdale, N.Y., USA). Cells were separated into soluble and insoluble fractions by centrifugation at 6,000 g for 5 min; the insoluble (pellet) fraction was then solubilized in 400 μl lysis buffer containing 8 M urea. The 400 μl fractions to be purified were transferred 200 μl at a time to a 96-well micro-titer plate containing 20-μl Ni-NTA magnetic-agarose beads, mixed for 1 min, placed on a 96-well magnet for 1 min, and the supernatant discarded before the remaining 200 μl was added. The beads were washed with 200 μl lysis buffer and the His-tagged proteins eluted with 35 μl of lysis buffer containing 1 M imidazole after placing the micro-titer plate on the magnet for 1 min. The levels of protein expression in the soluble and insoluble fractions following centrifugation and purification were estimated by comparison to a range of known protein concentration standards run in parallel using SDS-PAGE and visualized following staining with Coomassie blue. Purification of proteins from cultures of *E. coli* or insect cells grown in flasks was performed as described in Example 2.

Figure 4:
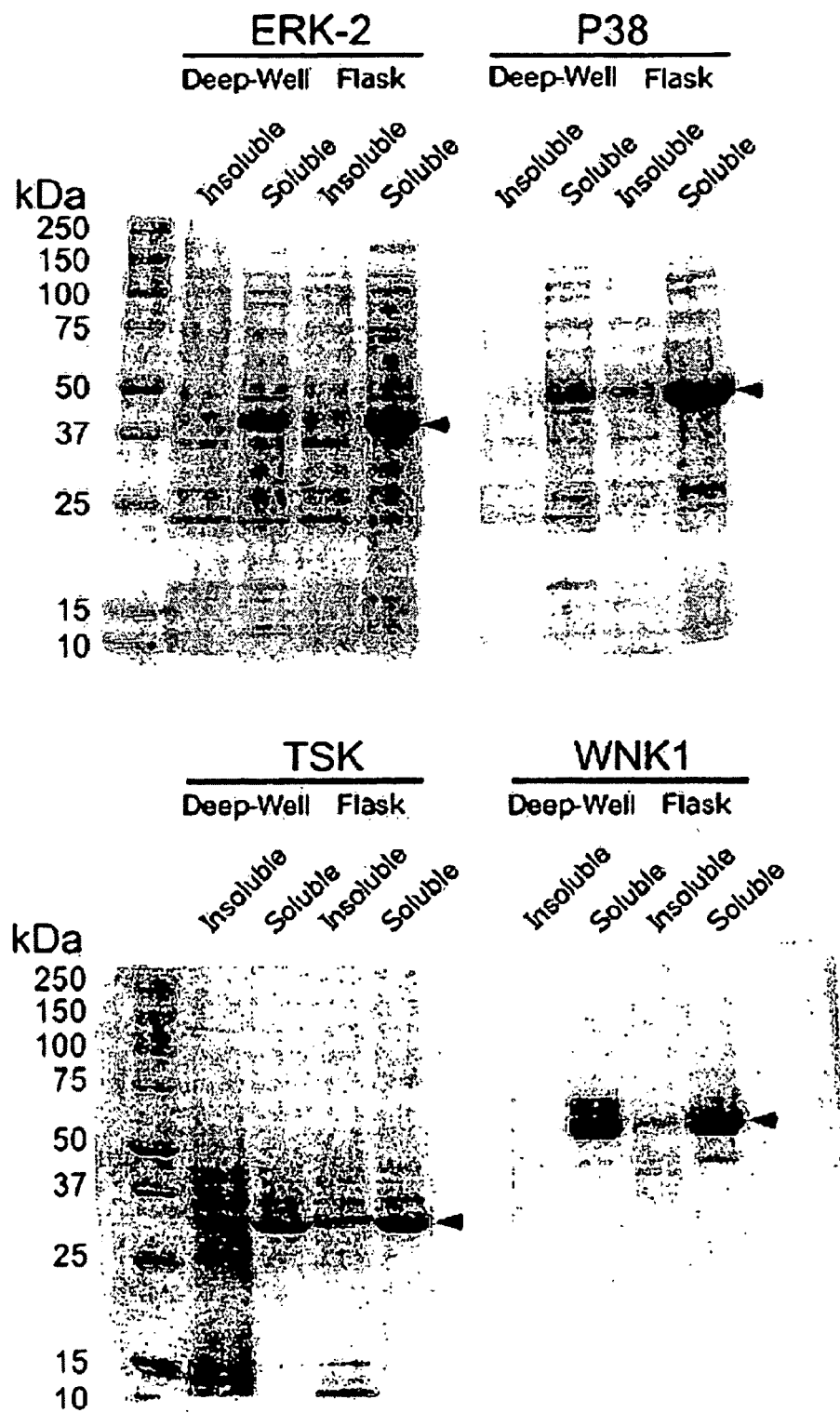
FIG. 4 shows SDS-PAGE analysis of expression of a variety of different kinases using the pBEV expression vector in *E. coli* and insect cells. Full-length Extracellular signal-regulated kinase 2 (ERK-2), Mitogen-activated protein kinase p38α (P38) were expressed and purified from 5 ml *E. coli* cultures grown in 24-well blocks and 2 l shake flasks (5 ml extracted from a 1 liter culture). Truncated T-cell specific kinase (TSK: G354-L620) and With No K (lysine)-1 (WNK1: P180-G602) were expressed and purified from 2 ml High-5 insect cell cultures infected and grown in 24-well blocks and 2.8 liter shake flasks (2 ml extracted from 700 ml cultures). Insoluble and insoluble fractions were analyzed for expression and recombinant protein identified.

Purification from equal volumes of cells allowed a direct comparison between the soluble expression in 24-well blocks and flasks for both *E. coli* and insect cells. As illustrated by the Coomassie-stained gel shown in FIG. 4, results indicate that the expression levels and solubility of recombinant proteins expressed in *E. coli* and insect cells are comparable whether produced in shake flask or a 24-well block. In examining hundreds of proteins it has consistently been found that proteins expressed and soluble in the 24-well blocks were subsequently re-confirmed as soluble when production was scaled up.

The levels of protein expressed and purified from the soluble or insoluble fractions of *E. coli* and insect cells grown in a deep-well block ranged from 0.1 μg/ml, detected using antibodies recognizing the His-tag epitope, to 20-80 μg/ml, which was readily identified on a Coomassie-stained gel.

Example 5

High Throughput Screening for Expression and Solubility

Small scale culture of *E. coli* and insect cells expressing recombinant proteins and grown in parallel offers a high throughput approach to screening, which facilitates the rapid identification of appropriate host cell and purification techniques and the rapid determination of solubility and other characteristics. The high-throughput expression platform was used for the parallel production of 62 full-length human kinases (non-receptor type), ranging in sizes from 35-163 kDa, cloned into pBEV and expressed in *E. coli* and insect cells. Briefly, cDNAs encoding the various kinases were cloned into pBEV between the NdeI and BamHI sites. The resulting expression vectors were transformed into *E. coli* and were also used to generate recombinant baculoviruses as described in the preceding examples. Recombinant baculoviruses were used to infect High-5 cells. *E. coli* and insect cells expressing the kinases were cultured in 24-well blocks and proteins harvested and purified as described above.

Figure 5:
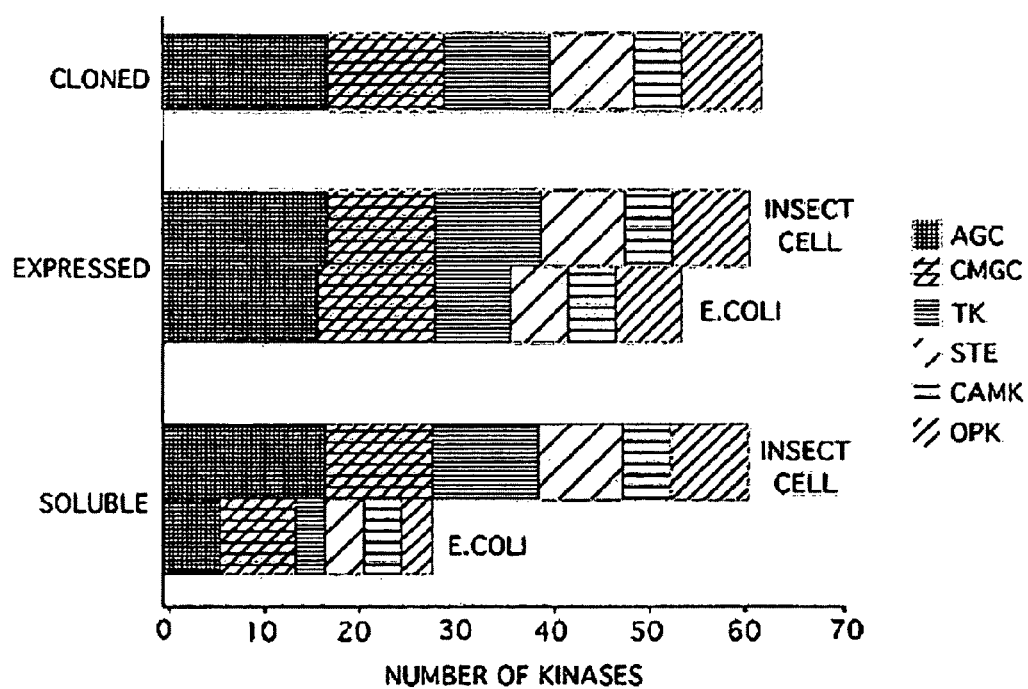
FIG. 5 shows a histogram of kinases cloned, expressed and soluble in *E. coli* and insect cells. The legend is indicated on the figure.

Kinases examined in this study fall into 6 major groups, bases on sequence and structural similarities, within the kinase superfamily. They are (1) AGC containing PKA, PKG, PKC families; (2) CAMK—Calcium/calmodiulin-dependent protein kinase; (3) CK1—Casein kinase-1; (4) CMGC containing CDK, MAPK, GSK, CLK families; (5) STE homologs; (6) TK—Tyrosine kinase (including Tyrosine-like kinase). The remainder OPK—Other protein kinases comprise those not falling into previous major groups. [31]. FIG. 5 is a histogram showing the number and classification of kinases that were cloned (upper portion of figure), expressed (middle portion of figure), and soluble (lower portion of figure) in *E. coli* cells and in insect cells.

Screening for expression and solubility in either expression system identified those proteins that were successfully expressed and soluble, which were readily distinguishable from those that either failed to express, were insoluble, or exhibited partial solubility. The definitions employed for expression and solubility allowed easy classification of the screening results. Successful expression was defined as protein production at or greater than 0.1 mg/ml: yields below this level were considered to be below the limit for practical purification in either native or denaturing conditions. The solubility of expressed proteins was classified into 3 categories. The first, termed soluble, resulted in the majority of expressed protein being found in the soluble fraction following fractionation. The second termed partially soluble, with protein distributed equally between the soluble and insoluble fractions. The last category, termed insoluble, had the bulk of the protein expressed found in the insoluble fraction following expression and purification.

In screening 62 kinases, while the majority were successfully expressed in *E. coli*, many were not expressed in a soluble form and were incapable of being purified in their native state. Of the 54 proteins (87%) expressed in *E. coli* only 29 proteins (54%) were soluble, with the remaining 25 (46%), either insoluble or exhibiting only partial solubility. Within the larger kinase superfamilies examined there appears to be a trend towards greater soluble expression in *E. coli* in the following order: TK>AGC>STE>>CMGC>CAMK.

Various previous studies describing attempts to develop high throughput technologies for protein production have used bacterial proteins having molecular weights<23 kDa. Most of these proteins are cytoplasmic and, not surprisingly, are soluble when expressed in *E. coli* [26], and, in the case of thermophilic bacterial proteins, are robustly expressed [27]. This bias has resulted in a 46-93% success rate obtaining soluble expression of prokaryotic proteins in *E. coli* [26] compared with 13% soluble expression of eukaryotic proteins in *E. coli* [28]. The numbers reflect the close phylogenetic relationship between protein source and expression host. The complexity of eukaryotic proteins would appear best served when produced in eukaryotic hosts, e.g., using yeast [10] or insect cells [12]. In the expression screen of 62 human kinases in insect cells, described herein, all but one of the kinases screened were expressed and soluble. The 99% success rate achieved in expressing human kinases in insect cells is significantly higher than the 54% success rate achieved when expressing the same proteins in *E. coli* and demonstrates the benefit of insect cells in the production of eukaryotic proteins.

Figure 6:
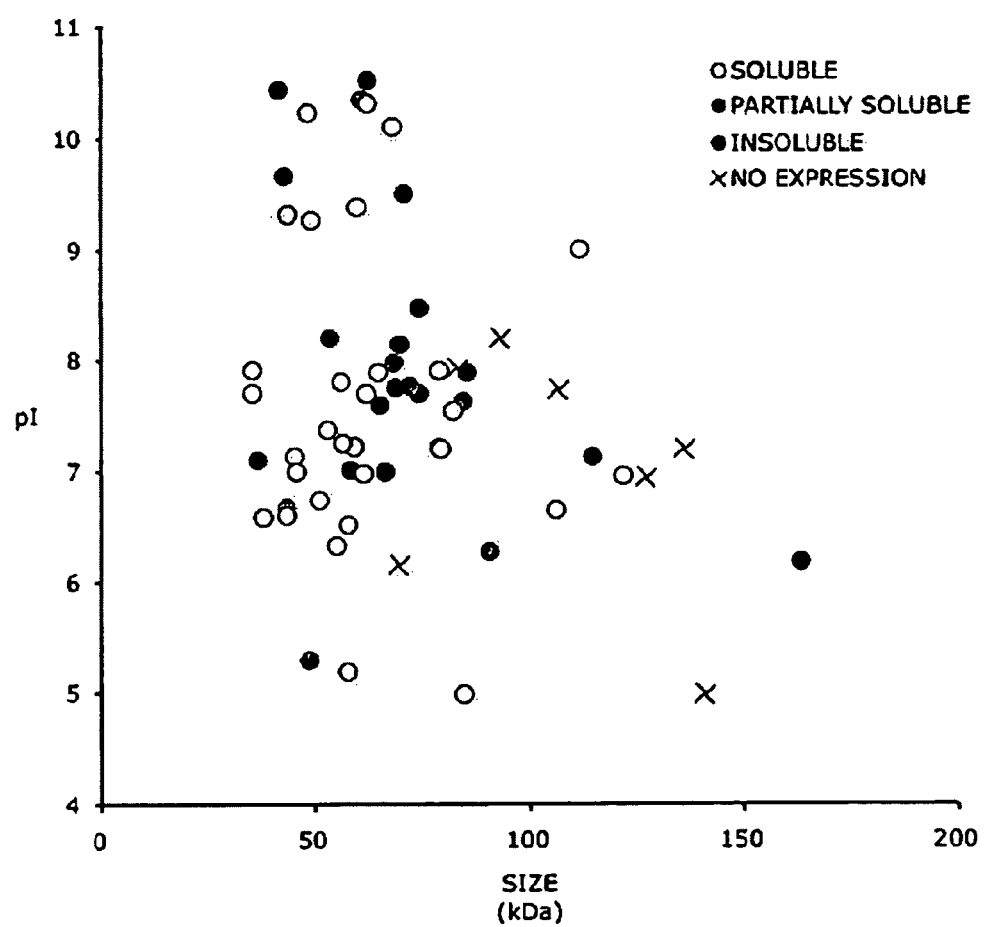
FIG. 6 is a scatter plot of kinases expressed in *E. coli*, based on their predicted molecular weight and isoelectric point. The plot identifies kinase expression resulting in soluble (○), partially soluble (◉) insoluble (●) and no expression (X).
Figure 7A:
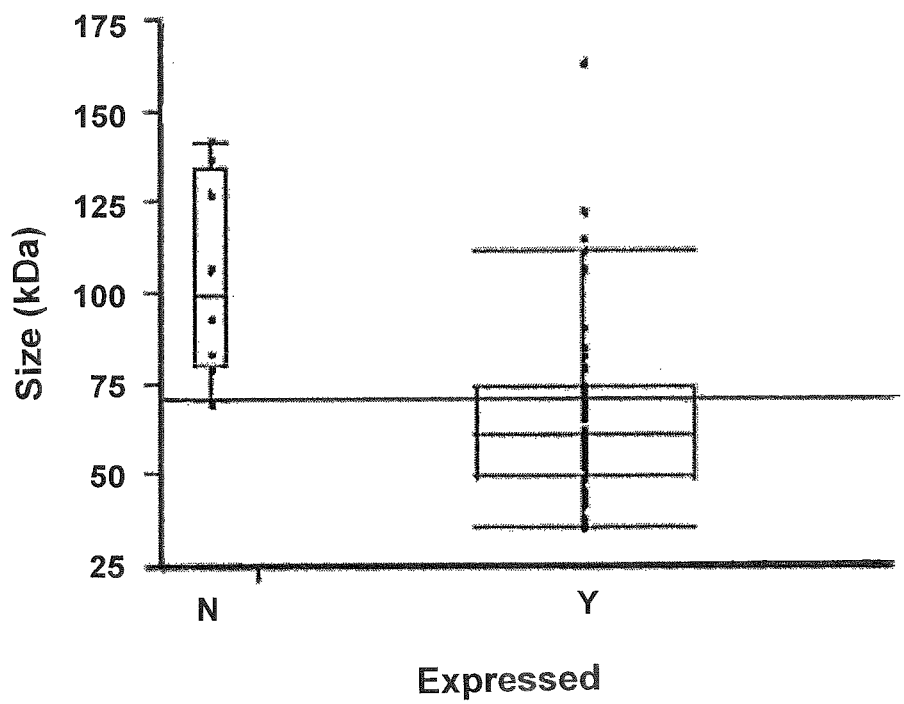
FIG. 7 presents data analysis of expression and solubility in *E. coli*. Analysis revealed correlation between protein size, its ability to be expressed (FIG. 7A) and its solubility (FIG. 7B) in *E. coli*. Protein solubility identified as soluble (Y), partially soluble (P) and insoluble (N). Statistical analysis performed using JMP-4 software (SAS Institute Inc., Cary, N.C., USA).
Figure 7B:
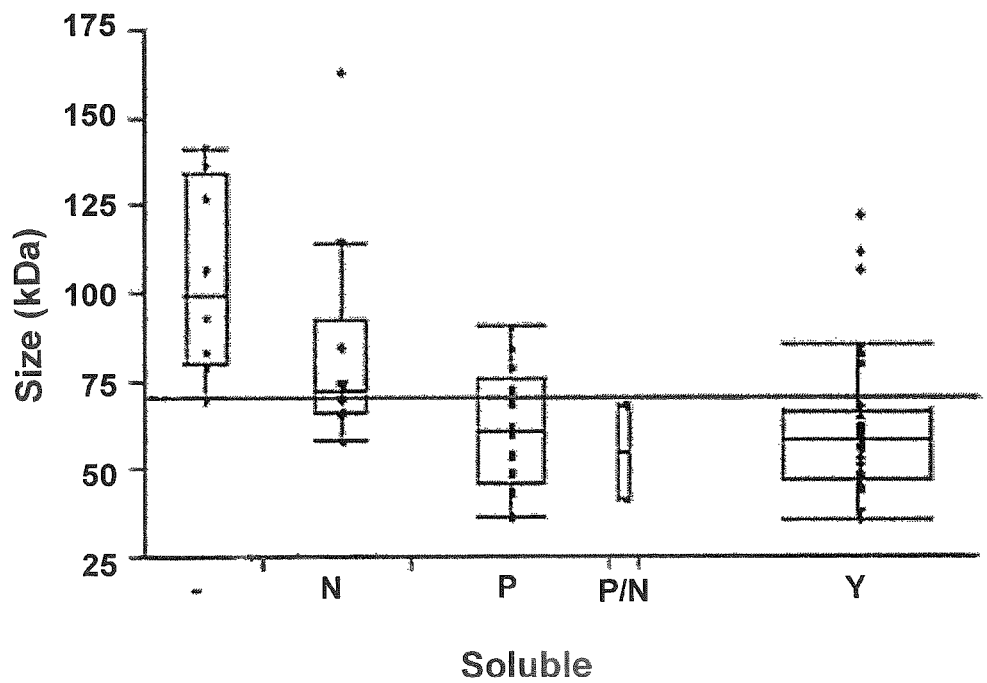

The variability in expression and protein solubility exhibited in *E. coli* provided data from which to identify biophysical characteristics potentially responsible for any differences in protein expression and solubility. The molecular weight and pI of full-length kinases (including His-tag) were calculated from their DNA sequence. FIG. 6 is a histogram on which the proteins are plotted based on molecular weight and pI and are identified with respect to their solubility. Analysis of the data generated by the *E. coli* expression screen revealed a correlation between successful expression in *E. coli* and decreasing protein size (FIG. 7A); this had been previously observed in the expression of human proteins in *E. coli* [29]. Protein solubility in *E. coli* also appeared directly related to the size of the protein expressed (FIG. 7B), with a preference for proteins<50 kDa being soluble. Reduction in expression and solubility with protein size has been observed in the expression of the thermophilic bacterium *Thermotoga maritima* genome in *E. coli* [30]. This limitation of *E. coli* expression will likely have significant consequences in terms of the utility of bacterial expression of the human genome. With an average molecular weight of 52 kDa [31] the majority of the human proteome produced in *E. coli* may insoluble, if expressed at all.

To further analyze the data, codon adaptive index (CAI) for *E. coli* and insect cells expression was calculated using EMBOSS [18]. The Wilkinson-Harrison solubility model was used to predict the solubility of proteins expressed in *E. coli* [19]. Of the eight proteins that failed to express in *E. coli* in this study, four were large proteins (>100 kDa) containing a high proportion of rare *E. coli* codons. The accompanying low CAI is often cited for failed or low expression of mammalian genes in *E. coli* [32]. The remaining four that failed to express in *E. coli* were moderately sized proteins (<100 kDa) with higher CAI values, suggesting other factor(s) also impact expression efficiency. The only kinase that failed to express in insect cells was DYRK3, a moderately sized protein (67.9 kDa) with a high pI (10.12), which was successfully expressed and soluble in *E. coli*.

The experimental results also failed to conform to the Wilkinson-Harrison model, based on protein parameters, proposed to predict soluble expression in *E. coli* [19]. Equally confounding was the lack of accuracy of the CAI in determining successful expression in either *E. coli* or insect cells. The strategy of parallel processing of *E. coli* and insect cell expression, rapidly generating empirical data, allows the identification of the most tractable protein and expression system. Subsequently, comparative analysis of the expression data can be used for both target prioritization in production and downstream to ensure the maximum efficiency of resources. Although many proteins were not soluble when expressed in the *E. coli* expression system this disadvantage was counterbalanced by the ability to identify those proteins that were soluble and well-expressed proteins in *E. coli* by screening. This tactic enables *E. coli*, with its various advantages for protein production, to make an important contribution to protein production and confirms the utility of the parallel approach. pBEV, and its accompanying expression platform, has been successfully deployed to express thousands of cDNAs in *E. coli* and insect cells, successfully generating hundreds of proteins for both enzyme characterization [33] and structure determination [34] [35] [36].

Equivalents

Those skilled in the art will recognize, or be able to ascertain using no more than routine experimentation, many equivalents to the specific embodiments of the invention described herein. The scope of the present invention is not intended to be limited to the above Description, but rather is as set forth in the claims that follow the reference list Reference List 1. A. Lueking, C. Holz, C. Gotthold, H. Lehrach, and D. Cahill, A system for dual protein expression in *Pichia pastoris* and *Escherichia coli*, Protein Expr Purif 20 (2000) 372-378.
2. R. Novy, K. Yaeger, S. Monsma, and M. Scott, in InNovations, 1999 pp. 1-5.
3. A. J. Walhout, G. F. Temple, M. A. Brasch, J. L. Hartley, M. A. Lorson, S. van den Heuvel, and M. Vidal, GATEWAY recombinational cloning: application to the cloning of large numbers of open reading frames or ORFeomes, Methods Enzymol 328 (2000) 575-592.
4. Q. Liu, M. Z. Li, D. Leibham, D. Cortez, and S. J. Elledge, The univector plasmid-fusion system, a method for rapid construction of recombinant DNA without restriction enzymes, Curr Biol 8 (1998) 1300-1309.
5. F. A. Marston, The purification of eukaryotic polypeptides synthesized in *Escherichia coli*, Biochem J 240 (1986) 1-12.
6. J. M. Vlak, and R. J. Keus, Baculovirus expression vector system for production of viral vaccines, Adv Biotechnol Processes 14 (1990) 91-128.
7. R. Wetzel, L. J. Perry, and C. Veilleux, Mutations in human interferon gamma affecting inclusion body formation identified by a general immunochemical screen, Biotechnology (N Y) 9 (1991) 731-737.
8. R. K. Knaust, and P. Nordlund, Screening for soluble expression of recombinant proteins in a 96-well format, Anal Biochem 297 (2001) 79-85.
9. K. Bussow, E. Nordhoff, C. Lubbert, H. Lehrach, and G. Walter, A human cDNA library for high-throughput protein expression screening, Genomics 65 (2000) 1-8.
10. C. Holz, O. Hesse, N. Bolotina, U. Stahl, and C. Lang, A micro-scale process for high-throughput expression of cDNAs in the yeast *Saccharomyces cerevisiae*, Protein Expr Purif 25 (2002) 372-378.
11. J. A. Heyman, J. Cornthwaite, L. Foncerrada, J. R. Gilmore, E. Gontang, K. J. Hartman, C. L. Hernandez, R. Hood, H. M. Hull, W. Y. Lee, R. Marcil, E. J. Marsh, K. M. Mudd, M. J. Patino, T. J. Purcell, J. J. Rowland, M. L. Sindici, and J. P. Hoeffler, Genome-scale cloning and expression of individual open reading frames using topoisomerase I-mediated ligation, Genome Res 9 (1999) 383-392.
12. J. S. Albala, K. Franke, I. R. McConnell, K. L. Pak, P. A. Folta, B. Rubinfeld, A. H. Davies, G. G. Lennon, and R. Clark, From genes to proteins: high-throughput expression and purification of the human proteome, J Cell Biochem 80 (2000) 187-191.
13. F. W. Studier, and B. A. Moffatt, Use of bacteriophage T7 RNA polymerase to direct selective high-level expression of cloned genes, J Mol Biol 189 (1986) 113-130.
14. G. E. Smith, M. D. Summers, and M. J. Fraser, Production of human beta interferon in insect cells infected with a baculovirus expression vector, Mol Cell Biol 3 (1983) 2156-2165.
15. S. P. Chambers, J. K. Brehm, N. P. Michael, T. Atkinson, and N. P. Minton, Physical characterisation and over-expression of the *Bacillus* caldotenax superoxide dismutase gene, FEMS Microbiol Lett 70 (1992) 277-284.
16. F. W. Studier, Use of bacteriophage T7 lysozyme to improve an inducible T7 expression system, J Mol Biol 219 (1991) 37-44.
17. A. I. Derman, W. A. Prinz, D. Belin, and J. Beckwith, Mutations that allow disulfide bond formation in the cytoplasm of *Escherichia coli*, Science 262 (1993) 1744-1747.
18. P. Rice, I. Longden, and A. Bleasby, EMBOSS: the European Molecular Biology Open Software Suite, Trends Genet. 16 (2000) 276-277.
19. D. L. Wilkinson, and R. G. Harrison, Predicting the solubility of recombinant proteins in *Escherichia coli*, Biotechnology (N Y) 9 (1991) 443-448.
20. S. M. Thiem, and L. K. Miller, Identification, sequence, and transcriptional mapping of the major capsid protein gene of the baculovirus *Autographa californica* nuclear polyhedrosis virus, J Virol 63 (1989) 2008-2018.
21. Y. W. Hu, and C. Y. Kang, Enzyme activities in four different forms of human immunodeficiency virus 1 pol gene products, Proc Natl Acad Sci USA 88 (1991) 4596-4600.
22. B. G. Ooi, C. Rankin, and L. K. Miller, Downstream sequences augment transcription from the essential initiation site of a baculovirus polyhedrin gene, J Mol Biol 210 (1989) 721-736.
23. V. A. Luckow, and M. D. Summers, High level expression of nonfused foreign genes with *Autographa californica* nuclear polyhedrosis virus expression vectors, Virology 170 (1989) 31-39.
24. D. R. O'Reilly, L. K. Miller, and V. A. Luckow, Baculovirus Expression Vectors: a Laboratory Manual, ed., W. H. Freeman and Co., New York 1992.
25. V. Tsakraklides, and M. J. Solomon, Comparison of Caklp-like cyclin-dependent kinase-activating kinases, J Biol Chem 277 (2002) 33482-33489.
26. A. Yee, X. Chang, A. Pineda-Lucena, B. Wu, A. Semesi, B. Le, T. Ramelot, G. M. Lee, S. Bhattacharyya, P. Gutierrez, A. Denisov, C. H. Lee, J. R. Cort, G. Kozlov, J. Liao, G. Finak, L. Chen, D. Wishart, W. Lee, L. P. McIntosh, K. Gehring, M. A. Kennedy, A. M. Edwards, and C. H. Arrowsmith, An NMR approach to structural proteomics, Proc Natl Acad Sci USA 99 (2002) 1825-1830.
27. D. Christendat, A. Yee, A. Dharamsi, Y. Kluger, A. Savchenko, J. R. Cort, V. Booth, C. D. Mackereth, V. Saridakis, I. Ekiel, G. Kozlov, K. L. Maxwell, N. Wu, L. P. McIntosh, K. Gehring, M. A. Kennedy, A. R. Davidson, E. F. Pai, M. Gerstein, A. M. Edwards, and C. H. Arrowsmith, Structural proteomics of an archaeon, Nat Struct Biol 7 (2000) 903-909.
28. P. Braun, Y. Hu, B. Shen, A. Halleck, M. Koundinya, E. Harlow, and J. LaBaer, Proteome-scale purification of human proteins from bacteria, Proc Natl Acad Sci USA 99 (2002) 2654-2659.
29. H. T. Ding, H. Ren, Q. Chen, G. Fang, L. F. Li, R. Li, Z. Wang, X. Y. Jia, Y. H. Liang, M. H. Hu, Y. Li, J. C. Luo, X. C. Gu, X. D. Su, M. Luo, and S. Y. Lu, Parallel cloning, expression, purification and crystallization of human proteins for structural genomics, Acta Crystallogr D Biol Crystallogr 58 (2002) 2102-2108.
30. S. A. Lesley, P. Kuhn, A. Godzik, A. M. Deacon, I. Mathews, A. Kreusch, G. Spraggon, H. E. Klock, D. McMullan, T. Shin, J. Vincent, A. Robb, L. S. Brinen, M. D. Miller, T. M. McPhillips, M. A. Miller, D. Scheibe, J. M. Canaves, C. Guda, L. Jaroszewski, T. L. Selby, M. A. Elsliger, J. Wooley, S. S. Taylor, K. O. Hodgson, I. A. Wilson, P. G. Schultz, and R. C. Stevens, Structural genomics of the *Thermotoga maritima* proteome implemented in a high-throughput structure determination pipeline, Proc Natl Acad Sci USA 99 (2002) 11664-11669.
31. E. S. Lander, L. M. Linton, B. Birren, C. Nusbaum, M. C. Zody, J. Baldwin, K. Devon, K. Dewar, M. Doyle, W. FitzHugh, R. Funke, D. Gage, K. Harris, A. Heaford, J. Howland, L. Kann, J. Lehoczky, R. LeVine, P. McEwan, K. McKernan, J. Meldrim, J. P. Mesirov, C. Miranda, W. Morris, J. Naylor, C. Raymond, M. Rosetti, R. Santos, A. Sheridan, C. Sougnez, N. Stange-Thomann, N. Stojanovic, A. Subramanian, D. Wyman, J. Rogers, J. Sulston, R. Ainscough, S. Beck, D. Bentley, J. Burton, C. Clee, N. Carter, A. Coulson, R. Deadman, P. Deloukas, A. Dunham, I. Dunham, R. Durbin, L. French, D. Grafham, S. Gregory, T. Hubbard, S. Humphray, A. Hunt, M. Jones, C. Lloyd, A. McMurray, L. Matthews, S. Mercer, S. Milne, J. C. Mullikin, A. Mungall, R. Plumb, M. Ross, R. Shownkeen, S. Sims, R. H. Waterston, R. K. Wilson, L. W. Hillier, J. D. McPherson, M. A. Marra, E. R. Mardis, L. A. Fulton, A. T. Chinwalla, K. H. Pepin, W. R. Gish, S. L. Chissoe, M. C. Wendl, K. D. Delehaunty, T. L. Miner, A. Delehaunty, J. B. Kramer, L. L. Cook, R. S. Fulton, D. L. Johnson, P. J. Minx, S. W. Clifton, T. Hawkins, E. Branscomb, P. Predki, P. Richardson, S. Wenning, T. Slezak, N. Doggett, J. F. Cheng, A. Olsen, S. Lucas, C. Elkin, E. Uberbacher, M. Frazier, et al., Initial sequencing and analysis of the human genome, Nature 409 (2001) 860-921.
32. S. P. Zhang, G. Zubay, and E. Goldman, Low-usage codons in *Escherichia coli*, yeast, fruit fly and primates, Gene 105 (1991) 61-72.
33. C. H. Gross, J. D. Parsons, T. H. Grossman, P. S. Charifson, S. Bellon, J. Jernee, M. Dwyer, S. P. Chambers, W. Markland, M. Botfield, and S. A. Raybuck, Active-Site Residues of *Escherichia coli* DNA Gyrase Required in Coupling ATP Hydrolysis to DNA Supercoiling and Amino Acid Substitutions Leading to Novobiocin Resistance, Antimicrob Agents Chemother 47 (2003) 1037-1046.
34. E. ter Haar, J. T. Coll, D. A. Austen, H. M. Hsiao, L. Swenson, and J. Jain, Structure of GSK3beta reveals a primed phosphorylation mechanism, Nat Struct Biol 8 (2001) 593-596.
35. G. M. Cheetham, R. M. Knegtel, J. T. Coll, S. B. Renwick, L. Swenson, P. Weber, J. A. Lippke, and D. A. Austen, Crystal structure of aurora-2, an oncogenic serine/threonine kinase, J Biol Chem 277 (2002) 42419-42422.
36. W. Meng, L. L. Swenson, M. J. Fitzgibbon, K. Hayakawa, E. Ter Haar, A. E. Behrens, J. R. Fulghum, and J. A. Lippke, Structure of mitogen-activated protein kinase-activated protein (MAPKAP) kinase 2 suggests a bifunctional switch that couples kinase activation with nuclear export, J Biol Chem 277 (2002) 37401-37405.
37. del Solar, G., et al. Microbiol and Mol Biol Rev, 62(2), pp. 434-464, 1998.
38. Beames, B., Braunagel, S., Summers, M. D. & Lanford, R. E., Polyhedron initiator codon altered to AUU yields unexpected fusion protein from baculovirus vector. Biotechniques 11: 378-383, 1991.
39. Luknow V. A. & Summers, M. D., High level expression of non-fused foreign genes with *Autographa californica* nuclear polyhedrosis virus gene expression vector. Virology 170:31-39, 1989.

I claim:

1. A kit comprising a vector for expressing a protein in bacterial and insect host cells, the vector comprising:
   first and second promoters, wherein the first promoter is effective to express a downstream protein coding sequence in insect host cells and the second promoter is effective to express the same downstream protein coding sequence in bacterial host cells; and
   a cloning site downstream of the promoters such that a protein coding sequence inserted into the site is transcribed in insect host cells and in bacterial host cells,
   wherein the second promoter is located between the first promoter and the cloning site, and
   the distance between the 3' end of the second promoter and a ribosome binding site (RBS) is less than 100 nucleotides;
   further comprising at least one item selected from the group consisting of: bacterial host cells, insect host cells, baculovirus DNA, transfection reagent, agarose, an inducer, a restriction enzyme, a ligation mix, culture medium, an antibody, a buffer, a control plasmid, and instructions for use.

2. A method of producing a protein of interest comprising steps of:
   inserting a polynucleotide encoding a protein of interest into a cloning site of a vector for expressing a protein in bacterial and insect host cells, the vector comprising:
      first and second promoters, wherein the first promoter is effective to express a downstream protein coding sequence in insect host cells and the second promoter is effective to express the same downstream protein coding sequence in bacterial host cells; and
      a cloning site downstream of the promoters such that a protein coding sequence inserted into the site is transcribed in insect host cells and in bacterial host cells,
      wherein the second promoter is located between the first promoter and the cloning site, and
      the distance between the 3' end of the second promoter and a ribosome binding site (RBS) is less than 100 nucleotides;
   introducing the resulting vector, or a recombinant baculovirus derived from the vector into a host cell;
   culturing the host cell under conditions in which the protein is expressed; and
   harvesting the protein.

3. The method of claim 2, wherein the host cell is an insect cell or a bacterial cell.

4. The kit of claim 1, wherein the first promoter is the baculovirus polh promoter.

5. The method of claim 2, wherein the first promoter is the baculovirus polh promoter.

6. The method of claim 5, wherein the host cell is an insect cell or a bacterial cell.

7. A kit comprising a vector for expressing a protein in bacterial and insect host cells, the vector comprising:
   first and second promoters, wherein the first promoter is a baculovirus polh promoter effective to express a downstream protein coding sequence in insect host cells expressing baculovirus proteins and the second promoter is effective to express the same downstream protein coding sequence in bacterial host cells; and
   a cloning site downstream of the promoters such that a protein coding sequence inserted into the site is transcribed in insect host cells expressing baculovirus proteins and in bacterial host cells,
   wherein the portion of the vector between the polh promoter and the cloning site comprises at least a portion of the polh mRNA 5' untranslated region, and wherein the portion of the polh mRNA 5' untranslated region is not immediately followed by a portion encoding a 5' portion of the Polh protein;
   further comprising at least one item selected from the group consisting of: bacterial host cells, insect host cells, baculovirus DNA, transfection reagent, agarose, an inducer, a restriction enzyme, a ligation mix, culture medium, an antibody, a buffer, a control plasmid, and instructions for use.

8. A method of producing a protein of interest comprising steps of:
   inserting a polynucleotide encoding a protein of interest into a cloning site of a vector for expressing a protein in bacterial and insect host cells, the vector comprising:
      first and second promoters, wherein the first promoter is a baculovirus polh promoter effective to express a downstream protein coding sequence in insect host cells expressing baculovirus proteins and the second promoter is effective to express the same downstream protein coding sequence in bacterial host cells; and a cloning site downstream of the promoters such that a protein coding sequence inserted into the site is transcribed in insect host cells expressing baculovirus proteins and in bacterial host cells, wherein the portion of the vector between the polh promoter and the cloning site comprises at least a portion of the polh mRNA 5' untranslated region, and wherein the portion of the polh mRNA 5' untranslated region is not immediately followed by a portion encoding a 5' portion of the Polh protein;

introducing the resulting vector, or a recombinant baculovirus derived from the vector into a host cell;

culturing the host cell under conditions in which the protein is expressed; and harvesting the protein.

9. The method of claim 8, wherein the host cell is an insect cell or a bacterial cell.

* * * * *

SEQUENCE LISTING

```
<160> NUMBER OF SEQ ID NOS: 4

<210> SEQ ID NO 1
<211> LENGTH: 315
<212> TYPE: DNA
<213> ORGANISM: Artificial
<220> FEATURE:
<223> OTHER INFORMATION: Shows and describes the sequence of a hybrid
      polh.

<400> SEQUENCE: 1
aaatgtctat caatatatag ttgctgatat catggagtaa ttaaaatgat aaccatctcg      60
caaataaata agtattttac gttttcgtaa cagttttgta ataaaaaaac tataaataat     120
acgactcact atagggggaat tgtgagcgga taacaattcc cctctagaaa taattttgtt    180
taactttaag aaggagatat accatgggca gcagccatca tcatcatcat cacagcagcg    240
gcctggtgcc gcgcggcagc catatgctcg aggatccctg caggcctcga gttcgaatct    300
agaagatctg gtacc                                                      315

<210> SEQ ID NO 2
<211> LENGTH: 5690
<212> TYPE: DNA
<213> ORGANISM: Artificial
<220> FEATURE:
<223> OTHER INFORMATION: Shows the complete nucleotide sequence of pBEV.

<400> SEQUENCE: 2
aacggctccg cccactatta atgaaattaa aaattccaat tttaaaaaac gcagcaagag      60
aaacatttgt atgaaagaat gcgtagaagg aaagaaaaat gtcgtcgaca tgctgaacaa    120
caagattaat atgcctccgt gtataaaaaa aatattgaac gatttgaaag aaaacaatgt    180
accgcgcggc ggtatgtaca ggaagaggtt tatactaaac tgttacattg caaacgtggt    240
ttcgtgtgcc aagtgtgaaa accgatgttt aatcaaggct ctgacgcatt tctacaacca    300
cgactccaag tgtgtgggtg aagtcatgca tctttttaatc aaatcccaag atgtgtataa    360
accaccaaac tgccaaaaaa tgaaaactgt cgacaagctc tgtccgtttg ctggcaactg    420
caagggtctc aatcctattt gtaattattg aataataaaa caattataaa tgctaaattt    480
gttttttatt aacgatacaa accaaacgca acaagaacat ttgtagtatt atctataatt    540
gaaaacgcgt agttataatc gctgaggtaa tatttaaaat cattttcaaa tgattcacag    600
ttaatttgcg acaatataat tttatttta cataaactag acgccttgtc gtcttcttct    660
tcgtattcct tctctttttc attttctcc tcataaaaat taacatagtt attatcgtat    720
ccatatatgt atctatcgta tagagtaaat tttttgttgt cataaatata tatgtctttt    780
ttaatggggt gtatagtacc gctgcgcata gttttttctgt aatttacaac agtgctattt    840
tctggtagtt cttcggagtg tgttgcttta attattaaat ttatataatc aatgaatttg    900
ggatcgtcgg ttttgtacaa tatgttgccg gcatagtacg cagcttcttc tagttcaatt    960
acaccatttt ttagcagcac cggattaaca taactttcca aaatgttgta cgaaccgtta   1020
aacaaaaaca gttcacctcc cttttctata ctattgtctg cgagcagttg tttgttgtta   1080
```

```
aaaataacag ccattgtaat gagacgcaca aactaatatc acaaactgga aatgtctatc    1140
aatatatagt tgctgatatc atggagataa ttaaaatgat aaccatctcg caaataaata    1200
agtattttac tgttttcgta acagttttgt aataaaaaaa cctataaata atacgactca    1260
ctatagggga attgtgagcg ataacaatt ccctctaga aataattttg tttaacttta     1320
agaaggagat ataccatggg cagcagccat catcatcatc atcacagcag cggcctggtg    1380
ccgcgcggca gccatatgct cgaggatccc tgcaggcctc gagttcgaat ctagaagatc    1440
tggtaccgag ctcgaattcc cgggcggccg cttaattaat tgatccgggt tattagtaca    1500
tttattaagc gctagattct gtgcgttgtt gatttacaga caattgttgt acgtatttta    1560
ataattcatt aaatttataa tctttagggt ggtatgttag agcgaaaatc aaatgatttt    1620
cagcgtcttt atatctgaat ttaaatatta atcctcaat agatttgtaa aataggtttc     1680
gattagtttc aaacaagggt tgttttccg aaccgatggc tggactatct aatggatttt     1740
cgctcaacgc cacaaaactt gccaaatctt gtagcagcaa tctagctttg tcgatattcg    1800
tttgtgtttt gttttgtaat aaaggttcga cgtcgttcaa aatattatgc gcttttgtat    1860
ttctttcatc actgtcgtta gtgtacaatt gactcgacgt aaacacgtta aataaagctt    1920
ggacatattt aacatcgggc gtgttagctt tattaggccg attatcgtcg tcgtcccaac    1980
cctcgtcgtt agaagttgct tccgaagacg attttgccat agccacacga cgcctattaa    2040
ttgtgtcggc taacacgtcc gcgatcaaat ttgtagttga gcttttcgga attatttctg    2100
attgcgggcg ttttgggcg ggtttcaatc taactgtgcc cgattttaat tcagacaaca     2160
cgttagaaag cgatggtgca ggcggtggta acatttcaga cggcaaatct actaatggcg    2220
gcggtggtgg agctgatgat aaatctacca tcggtggagg cgcaggcggg gctggcggcg    2280
gaggcggagg cggaggtggt ggcggtgatg cagacggcgg tttaggctca aatgtctctt    2340
taggcaacac agtcggcacc tcaactattg tactggtttc gggcgccgtt tttggtttga    2400
ccggtctgag acgagtgcga ttttttttcgt ttctaatagc ttccaacaat tgttgtctgt    2460
cgtctaaagg tgcagcgggt tgaggttccg tcggcattgg tggagcgggc ggcaattcag    2520
acatcgatgg tggtggtggt ggtggaggcg ctggaatgtt aggcacggga aaggtggtg    2580 gcggcggtgc cgccggtata atttgttctg gtttagtttg ttcgcgcacg attgtgggca    2640
ccggcgcagg cgccgctggc tgcacaacgg aaggtcgtct gcttcgaggc agcgcttggg    2700
gtggtggcaa ttcaatatta taattggaat acaaatcgta aaaatctgct ataagcattg    2760
taatttcgct atcgtttacc gtgccgatat ttaacaaccg ctcaatgtaa gcaattgtat    2820
tgtaaagaga ttgtctcaag ctcggatcga tcccgcacgc cgataacaag ccttttcatt    2880
tttactacag cattgtagtg gcgagacact tcgctgtcgt cgcctgatgc ggtattttct    2940
ccttacgcat ctgtgcggta tttcacaccg catacgtcaa agcaaccata gtacgcgccc    3000
tgtagcggcg cattaagcgc ggcgggtgtg gtggttacgc gcagcgtgac cgctacactt    3060
gccagcgccc tagcgcccgc tcctttcgct ttcttccctt cctttctcgc cacgttcgcc    3120
ggctttcccc gtcaagctct aaatcggggg ctccctttag ggttccgatt tagtgcttta    3180
cggcacctcg accccaaaaa acttgatttg ggtgatggtt cacgtagtgg gccatcgccc    3240
tgatagacgg ttttcgccc tttgacgttg gagtccacgt tctttaatag tggactcttg     3300
ttccaaactg gaacaacact caaccctatc tcgggctatt cttttgattt ataagggatt    3360
ttgccgattt cggcctattg gttaaaaaat gagctgattt aacaaaaatt taacgcgaat    3420
tttaacaaaa tattaacgtt tacaattta tggtgcactc tcagtacaat ctgctctgat     3480
```

```
gccgcatagt taagccagcc ccgacacccg ccaacacccg ctgacgcgcc ctgacgggct    3540
tgtctgctcc cggcatccgc ttacagacaa gctgtgaccg tctccgggag ctgcatgtgt    3600
cagaggtttt caccgtcatc accgaaacgc gcgagacgaa agggcctcgt gatacgccta    3660
tttttatagg ttaatgtcat gataataatg gtttcttaga cgtcaggtgg cacttttcgg    3720
ggaaatgtgc gcggaacccc tatttgttta ttttttctaaa tacattcaaa tatgtatccg    3780
ctcatgagac aataaccctg ataaatgctt caataatatt gaaaaggaa gagtatgagt    3840 attcaacatt tccgtgtcgc ccttattccc ttttttgcgg catttttgcct tcctgttttt    3900 gctcacccag aaacgctggt gaaagtaaaa gatgctgaag atcagttggg tgcacgagtg    3960
ggttacatcg aactggatct caacagcggt aagatccttg agagttttcg ccccgaagaa    4020
cgttttccaa tgatgagcac ttttaaagtt ctgctatgtg gcgcggtatt atcccgtatt    4080
gacgccgggc aagagcaact cggtcgccgc atacactatt ctcagaatga cttggttgag    4140
tactcaccag tcacagaaaa gcatcttacg gatggcatga cagtaagaga attatgcagt    4200
gctgccataa ccatgagtga taacactgcg gccaacttac ttctgacaac gatcggagga    4260
ccgaaggagc taaccgcttt tttgcacaac atggggatc atgtaactcg ccttgatcgt    4320
tgggaaccgg agctgaatga agccatacca aacgacgagc gtgacaccac gatgcctgta    4380
gcaatggcaa caacgttgcg caaactatta actggcgaac tacttactct agcttcccgg    4440
caacaattaa tagactggat ggaggcggat aaagttgcag gaccacttct gcgctcggcc    4500
cttccggctg gctggtttat tgctgataaa tctggagccg gtgagcgtgg gtctcgcggt    4560
atcattgcag cactggggcc agatggtaag ccctcccgta tcgtagttat ctacacgacg    4620
gggagtcagg caactatgga tgaacgaaat agacagatcg ctgagatagg tgcctcactg    4680
attaagcatt ggtaactgtc agaccaagtt tactcatata ctttagat tgatttaaaa    4740 cttcatttt aatttaaaag gatctaggtg aagatccttt ttgataatct catgaccaaa    4800
atcccttaac gtgagttttc gttccactga gcgtcagacc ccgtagaaaa gatcaaagga    4860
tcttcttgag atcctttttt tctgcgcgta atctgctgct tgcaaacaaa aaaaccaccg    4920
ctaccagcgg tggtttgttt gccggatcaa gagctaccaa ctcttttcc gaaggtaact    4980 ggcttcagca gagcgcagat accaaatact gtccttctag tgtagccgta gttaggccac    5040
cacttcaaga actctgtagc accgcctaca tacctcgctc tgctaatcct gttaccagtg    5100
gctgctgcca gtggcgataa gtcgtgtctt accgggttgg actcaagacg atagttaccg    5160
gataaggcgc agcggtcggg ctgaacgggg ggttcgtgca cacagcccag cttggagcga    5220
acgacctaca ccgaactgag atacctacag cgtgagctat gagaaagcgc cacgcttccc    5280
gaagggagaa aggcggacag gtatccggta agcggcaggg tcggaacagg agagcgcacg    5340
agggagcttc cagggggaaa cgcctggtat ctttatagtc ctgtcgggtt tcgccacctc    5400
tgacttgagc gtcgattttt gtgatgctcg tcagggggc ggagcctatg gaaaaacgcc    5460
agcaacgcgg cctttttacg gttcctggcc ttttgctggc cttttgctca catgttcttt    5520
cctgcgttat cccctgattc tgtggataac cgtattaccg cctttgagtg agctgatacc    5580
gctcgccgca gccgaacgac cgagcgcagc gagtcagtga gcgaggaagc ggaagagcgc    5640
ccaatacgca aaccgcctct ccccgcgcgt tggccgattc attaatgcag    5690
```

<210> SEQ ID NO 3
<211> LENGTH: 175
<212> TYPE: DNA
<213> ORGANISM: Artificial

```
<220> FEATURE:
<223> OTHER INFORMATION: Shows an example of a hybrid promoter region
      that includes a minimal polh promoter together with the polh 5'
      UTR located upstream of the T71aco promoter and an RBS.

<400> SEQUENCE: 3
atcatggagt aattaaaatg ataaccatct cgcaaataaa taagtatttt acgttttcgt      60
aacagttttg taataaaaaa actataaata atacgactca ctaggggga attgtgagcg     120 gataacaatt cccctctaga aataattttg tttaacttta agaaggagat atacc         175

<210> SEQ ID NO 4
<211> LENGTH: 89
<212> TYPE: DNA
<213> ORGANISM: Artificial
<220> FEATURE:
<223> OTHER INFORMATION: Shows an example of minimal polh promoter.

<400> SEQUENCE: 4
atcatggagt aattaaaatg ataaccatct cgcaaataaa taagtatttt acgttttcgt      60
aacagttttg taataaaaaa actataaat                                       89
```